United States Patent
Borchert et al.

(10) Patent No.: US 6,518,042 B1
(45) Date of Patent: Feb. 11, 2003

(54) PROCESS FOR MAKING DNA LIBRARIES IN FILAMENTOUS FUNGAL CELLS USING A NOVEL CLONED GENE INVOLVED IN THE MISMATCH REPAIR SYSTEM OF FILAMENTOUS FUNGAL CELLS

(75) Inventors: Torben Vedel Borchert, Copenhagen (DK); Lars Christiansen, deceased, late of Bagsvaerd (DK), by Dennis Holm Pedersen, executor; Jesper Vind, Lyngby (DK)

(73) Assignee: Novozymes A/S, Bagsvaerd (DK)

(*) Notice: Subject to any disclaimer, the term of this patent is extended or adjusted under 35 U.S.C. 154(b) by 0 days.

(21) Appl. No.: 09/512,250

(22) Filed: Feb. 24, 2000

Related U.S. Application Data

(60) Provisional application No. 60/121,840, filed on Feb. 26, 1999.

(30) Foreign Application Priority Data

Feb. 24, 1999 (DK) .......................... 1999 00253

(51) Int. Cl.[7] .......................... C12P 21/02; C12N 15/80; C12N 1/15; C07H 21/04

(52) U.S. Cl. .................. 435/69.1; 435/471; 435/254.11; 435/254.3; 435/254.7; 536/23.1

(58) Field of Search .................. 435/254.11, 254.3, 435/254.7, 6, 69.1, 471, 23.1; 536/23.1

(56) References Cited

FOREIGN PATENT DOCUMENTS

| EP | 0 449 923 B1 | | 10/1991 |
|---|---|---|---|
| WO | WO 90/07576 | * | 7/1990 |
| WO | WO 97/05268 | * | 2/1997 |
| WO | WO 97/37011 | * | 10/1997 |
| WO | WO 98/31837 | | 7/1998 |

OTHER PUBLICATIONS

Database SWISS–PROT, accession No. 013396, Huber, D.H. etal., DNA Mismatch Repair Protein MSH2, *Neurospora crassa*, (Dec. 15, 1998).

* cited by examiner

*Primary Examiner*—Remy Yucel
*Assistant Examiner*—Katharine F Davis
(74) *Attorney, Agent, or Firm*—Elias Lambiris; Jason Garbell

(57) ABSTRACT

A process for making DNA libraries in filamentous fungal cells using a novel cloned gene involved in the mismatch repair system of filamentous fungal cells.

18 Claims, 7 Drawing Sheets

Fig. 2

```
Contig# 1               •••••••••••   ••||•  •  ••  ••••|••••••••••••••• •|•••||••||•| |••••|•••••••••••
                                                                                      70

'msh2'Ao-col10          AQIGCFVPCTEAELTIFDCILARVGASDSQLKGVSTFMAEMLETSNILKSATSESLIIIDELGRGTSTYDGFGLAW
 (SEQ ID NO: 2)
'msh2'Ao-col13          AQIGCFVPCTEAELTIFDCILARVGASDSQLKGVSTFMAEMLETSNILKSATSESLIIIDELGRGTSTYDGFGLAW
 (SEQ ID NO: 2)
'msh2'Ao-col15          AQIGCFVPCTEAELTIFDCILARVGASDSQLKGVSTFMAEMLETSNILKSATSESLIIIDELGRGTSTYDGFGLAW
 (SEQ ID NO: 2)
msh2-human.p            AQIGCFVPCESAEVSIVDCILARVGAGDSQLKGVSTFMAEMLETASILRSATKDSLIIIDELGRGTSTYDGFGLAW
 (SEQ ID NO: 31)
S.c. msh2               AQIGCFVPCEEAEIAIVDAILCRVGAGDSQLKGVSTFMVEILETASILKNASKNSLIIVDELGRGTSTYDGFGLAW
 (SEQ ID NO: 32)
```

Fig 3 (a)

```
                       10        20        30        40        50        60
                        |         |         |         |         |         |
Contig# 1             •|    •    |   • •|  ||| ||   •|•| •|•• •|  • • |  • •| • ||||
S.c. msh2             MSSTRPELKFSDVSEERNFYKKYTGLPKKPLK-TIRLVDKGDYYTVIGSDAIFVADSVYHTQSVLK
(SEQ ID NO: 32)
Ao.MSH2               MSS-RPELKV-D—DEVGFIRFYRSLAANSNDETIRVFDRGDWYSAHGAKAEFIARTVYKTTSILR
(SEQ ID NO: 2)
msh2 mus.p            MAVQPKETLQLEGAAEAGFVRFFEGMPEKPST-TVRLFDRGDFYTAHGEDALLAAREVFKTQGVIK
(SEQ ID NO: 33)
msh2-human.p          MAVQPKETLQLESAAEVGFVRFFQGMPEKPTT-TVRLFDRGDFYTAHGEDALLAAREVFKTQGVIK
(SEQ ID NO: 31)
                       70        80        90       100       110       120       130
                        |         |         |         |         |         |         |
Contig# 1              ||   |   |    •|•  | |||| •|   ||•|         |• •   •••
S.c. msh2             NCQLDPVTAKNFHEPTKYVTVSLQVLATLLKLCLLDLGYKVEIY---------DKGWKLIKSASP
Ao.MSH2               N-LGRSDSGGLPS----VTMSVTVFRNFLREALFRLNKRIEIW----GSVGTGKGHWKLVKQASP
msh2 mus.p            Y-MGPAGSKTLQS----VVLSKMNFESFVKDLLLVRQYRVEVYKNKAGNKASKENEWYLAFKASP·
msh2-human.p          Y-MGPAGAKNLQS----VVLSKMNFESFVKDLLLVRQYRVEVYKNRAGNKASKENDWYLAYKASP
                              140       150       160       170       180       190
                               |         |         |         |         |         |
Contig# 1             ••|  ||| |      ||| |  ||•|    |    |•• |  •|    |•| || |•| |••|
S.c. msh2             GNIEQVNELM----NMNIDSSIIIASLKVQWNSQDGNCIIGVAFIDTTAYKVGMLDIVDNEVYSNL
Ao.MSH2               GNLQDVEEELGSVGGLSMDSAPIILAVKIS-AKAAEARSVGVCFADASVRELGVSEFLDNDIYSNF
msh2 mus.p            GNLSQFEDIL-FGNNDMSASVGVMGIKMA-VVDGQ-RHVGVGYVDSTQRKLGLCEFPENDQFSNL
msh2-human.p          GNLSQFEDIL-FGNNDMSASIGVVGVKMS-AVDGQ-RQVGVGYVDSIQRKLGLCEFPDNDQFSNL
```

Fig 3 (b)

```
                       200         210         220         230         240         250         260
                        |           |           |           |           |           |           |
Contig# 1          •|||••|• •••|             ||•|   |   •   ||      ||||••|  •• |••
S.c. msh2          ESFLIQLGVKECLVQDLTSNSNSNAEMQKVINVIDRCGCVVTLLKNSEFSEKDVELDLTKLL----
Ao.MSH2            ESLIIQLGVKECLVQ--MDANKKDVELGKIRAIADSCGIAISERPVADYGVKDIEQDLTRLLRDER
msh2 mus.p         EALLIQIGPKECV----LPGGETTGDMGKLRQVIQRGGILITERKRADFSTKDIYQDLNRLLKGKK
msh2-human.p       EALLIQIGPKECV----LPGGETAGDMGKLRQIIQRGGILITERKKADFSTKDIYQDLNRLLKGKK 270         280         290         300         310         320         330
                        |           |           |           |           |           |           |
Contig# 1             |    |  ••|   ||||||  |•|• |• ||||    •|||•      | ||•••• |•||••••
S.c. msh2          GDDL-ALSLPQKYSKLSMGACNALIGYLQLLSEQDQVGKYELVEHKLKEFMKLDASAIKALNLFPQ
Ao.MSH2            S----AGTLPQTELKLAMGSASALIKYLGVMTDPTNFGQYQLYQHDLSQFMKLDSSALRALNLMPG
msh2 mus.p         GEQINSAALPEMENQVAVSSLSAVIKFLELLSDDSNFGQFELATFDFSQYMKLDMAAVRALNLFQG
msh2-human.p       GEQMNSAVLPEMENQVAVSSLSAVIKFLELLSDDSNFGQFELTTFDFSQYMKLDIAAVRALNLFQG 340         350         360         370         380         390
                                   |           |           |           |           |           |
Contig# 1          | ||   •                    ••  •••  •••   • ••|  |•|••••   |  •| •  |••|
S.c. msh2          GPQNPFGSNNLAVSGFTSAGNSGKVTSLFQLLNHCKTNAGVRLLNEWLKQPLTNIDEINKRHDLVD
Ao.MSH2            PRDGSK-SM---------------SLFGLLNHCKTPVGSRLLAQWLKQPLMDLAEIEKRQQLVE
msh2 mus.p         SVEDTTGSQ---------------SLAALLNKCKTAQGQRLVNQWIKQPLMDRNRIEERLNLVE
msh2-human.p       SVEDTTGSQ---------------SLAALLNKCKTPQGQRLVNQWIKQPLMDKNRIEERLNLVE
```

Fig 3 (c)

```
                    400       410       420       430       440       450       460
                     |         |         |         |         |         |         |
Contig# 1          ||| ••••  |   |  •  |••| ••|•||||   ••|•   ||••    ||•  ||  |     |
S.c. msh2          YLIDQIELRQMLTSEYLPMIPDIRRLTKKLNKRG-NLEDVLKIYQFSKRIPEIVQVFTSFLEDDSP
Ao.MSH2            AFVVNTELRQTMQEEHLRSIPDLYRLAKRFQRKQANLEDVVRVYQVAIRLPGFVNSLENVMDEEYQ
msh2 mus.p         AFVEDSELRQSLQEDLLRRFPDLNRLAKKFQRQAANLQDCYRLYQGINQLPSVIQALEKY-EGRHQ
msh2-human.p       AFVEDAELRQTLQEDLLRRFPDLNRLAKKFQRQAANLQDCYRLYQGINQLPNVIQALEKH-EGKHQ 470       480       490       500       510       520
                     |         |         |         |         |         |
Contig# 1            | |    |•  ||•||••|•••|•|•   •  •|••||•   •| |•  | ||  •
S.c. msh2          TEPVNELVRSVWLAPLSHHVEPLSKFEEMVETTVDLDAYEENNEFMIKVEFNEELGKIRSKLDTLR
Ao.MSH2            T-----PLETEYTSNLRSHSDSLAKLEEMVETTVDLDALE-NHEFIIKPEFDESLRIIRKKLDKLR
msh2 mus.p         A-----LLLAVFVTPLIDLRSDFSKFQEMIETTLDMDQVE-NHEFLVKPSFDPNLSELREVMDGLE
msh2-human.p       K-----LLLAVFVTPLTDLRSDFSKFQEMIETTLDMDQVE-NHEFLVKPSFDPNLSELREIMNDLE 530       540       550       560       570       580       590
                     |         |         |         |         |         |         |
Contig# 1            |       •  |•|  •   •|| •||    •    •|•  ||    |•||||||     ••| •|
S.c. msh2          DEIHSIHLDSAEDLGFDPDKKLKLENHHLHGWCMRLTRNDAKELRKHKKYIELSTVKAGIFFSTKQ
Ao.MSH2            HDMGVEHRRVARDLDQDIEKKLFLENHRVHGWCFRLTRNESGCIRNKREYQECSTQKNGVYFTTST
msh2 mus.p         KKMQSTLINAARGLGLDPGKQIKLDSSAQFGYYFRVTCKEEKVLRNNKNFSTVDIQKNGVKFTNSE
msh2-human.p       KKMQSTLISAARDLGLDPGKQIKLDSSAQFGYYFRVTCKEEKVLRNNKNFSTVDIQKNGVKFTNSK
```

Figure 3 (d)

```
                    600        610        620        630        640        650        660
                     |          |          |          |          |          |          |
Contig# 1        | ||  •       |•|  •  ||•|•||•||  •    |  •  •|•|••  |  ••••  •  ••  ••  •
S.c. msh2        LKSIANETNILQKEYDKQQSALVREIINITLTYTPVFEKLSLVLAHLDVIASFAHTSSYAPIPYIR
Ao.MSH2          MQTLRREHDQLSSNYNRTQTGLVNEVVNVAASYCPVLERLAGVIAHLDVIVSFAHASVHAPTPYAR
msh2 mus.p       LSSLNEEYTKNKGEYEEAQDAIVKEIVNISSGYVEPMQTLNDVLAHLDAIVSFAHVSNAAPVPYVR
msh2-human.p     LTSLNEEYTKNKTEYEEAQDAIVKEIVNISSGYVEPMQTLNDVLAQLDAVVSFAHVSNGAPVPYVR 670        680        690        700        710        720
                             |          |          |          |          |          |
Contig# 1         •|   |      •   |••|  |•|••||•• •••  |    |   •  •••••••••••••••  •••
S.c. msh2         PKLHPMDSERRTHLISSRHPVLEMQDDISFISNDVTLESGKGDFLIITGPNMGGKSTYIRQVGVIS
Ao.MSH2           PKMHPRGTGNTV-LKEARHPCMEMQDDISFITNDVALVRDESSFLIITGPNMGGKSTYIRQIGVIA
msh2 mus.p        PVILEKGKGRII-LKASRHACVEVQDEVAFIPNDVHFEKDKQMFHIITGPNMGGKSTYIRQTGVIV
msh2-human.p      PAILEKGQGRII-LKASRHACVEVQDEIAFIPNDVYFEKDKQMFHIITGPNMGGKSTYIRQTGVIV 730        740        750        760        770        780        790
                       |          |          |          |          |          |          |
Contig# 1         ••••  ••••••   ••||•  •  ••  ••••|••••••••••••  •|•••||••||•|  |••••|•••••
S.c. msh2         LMAQIGCFVPCEEAEIAIVDAILCRVGAGDSQLKGVSTFMVEILETASILKNASKNSLIIVDELGR
Ao.MSH2           LMAQTGCFVPCTEAELTIFDCILARVGASDSQLKGVSTFMAEMLETSNILKSATSESLIIIDELGR
msh2 mus.p        LMAQIGCFVPCESAEVSIVDCILARVGAGDSQLKGVSTFMAEMLETSSILRSATKDSLIIIDELGR
msh2-human.p      LMAQIGCFVPCESAEVSIVDCILARVGAGDSQLKGVSTFMAEMLETASILRSATKDSLIIIDELGR
```

Figure 3 (e)

```
                     800        810        820        830        840        850
                      |          |          |          |          |          |
Contig# 1        ●●●●●●●●●●●●●●||  ●  |  ●    ●  |●●●●●●●●●  ●|||  ●    ●|●|●●  ●
S.c. msh2        GTSTYDGFGLAWAIAEHIASKIGCFALFATHFHELTELSEKLPN-VKNMHVVAHIEKNLKEQKHDD
Ao.MSH2          GTSTYDGFGLAWAISEHIVTEIRCFGLFATHFHELTALADRYPKSVKNLHVVAFIGDGTDDDSEDK
msh2 mus.p       GTSTYDGFGLAWAISDYIATKIGAFCMFATHFHELTALANQIP-TVNNLHVTALTTEET-------
msh2-human.p     GTSTYDGFGLAWAISEYIATKIGAFCMFATHFHELTALANQIP-TVNNLHVTALTTEET-------

860        870        880        890        900        910        920
                      |          |          |          |          |          |          |
Contig# 1                 |●|●●|●   ●|  ●●●●●●●●●●●|   ●●   ||   ●||●●  ●●|||
S.c. msh2        ----EDITLLYKVEPGISDQSFGIHVAEVVQFPEKIVKMAKRKANELDDLKTNNEDLK------KA
Ao.MSH2          KSKRNQVTLLYRVEPGICDQSFGIHVAELVRFPEKVVNMARQKAEELEDFTS-SEQQDQQSSMAID
msh2 mus.p       ------LTMLYQVKKGVCDQSFGIHVAELANFPRHVIACAKQKALELEEFQNIGTSLGCDEAEPAA
msh2-human.p     ------LTMLYQVKKGVCDQSFGIHVAELANFPKHVIECAKQKALELEEFQYIGESQGYDIMEPAA 930        940        950        960        970        980        990
                      |          |          |          |          |          |          |
Contig# 1         ●   ●|| ●    ||     |  ●●    |     ●     ●|     |     |     |   |
S.c. msh2        KLSLQEVNEGNIRLKALLKEWIRKVKEEGLHDPSKITEEASQHKIQELLRAIANEPEKENDNYLEI
Ao.MSH2          KYSQEEVEEGS----ALLKAMLLKWKSETE---SSGKELTVEEKRQIMRDLVKADEKLQANKVFQG
msh2 mus.p       KRRCLEREQGE----KIILEFLSKVKQVPF---TAMSEESISAKLKQLKAEVVAKNNSFVNEIISR
msh2-human.p     KKCYLEREQGE----KIIQEFLSKVKQMPF---TEMSEENITIKLKQLKAEVIAKNNSFVNEIISR Contig# 1         ●
S.c. msh2        YKSPCCYN
Ao.MSH2          IK--A--L
msh2 mus.p       IKAPA--P
msh2-human.p     IKV-T--T
```

PROCESS FOR MAKING DNA LIBRARIES IN FILAMENTOUS FUNGAL CELLS USING A NOVEL CLONED GENE INVOLVED IN THE MISMATCH REPAIR SYSTEM OF FILAMENTOUS FUNGAL CELLS

CROSS-REFERENCE TO RELATED APPLICATIONS

This application claims priority under 35 U.S.C. 119 of U.S. provisional application No. 60/121,840 filed Feb. 26, 1999 and Danish application no. PA 1999 00253 filed Feb. 24, 1999, the contents of which are fully incorporated herein by reference.

BACKGROUND OF THE INVENTION

1. Field of the Invention

A process for making DNA libraries in filamentous fungal cells using a novel cloned gene involved in the mismatch repair system of filamentous fungal cells.

2. Description of the Related Art

The mismatch repair system is a system within cells which recognizes mismatches in newly synthesized duplex DNA sequences.

The mismatch repair system then either corrects the mismatches which are seen as errors by e.g. using the methylated "old" strain as template or alternatively it may mediate degradation of the duplex DNA sequences which comprise the mismatches.

Independently on the precise mechanism the end result will be that the "mismatch repair system" will limit the "diversity" within a cell, diversity being represented as duplex DNA sequences which comprise mismatches.

For example a duplex DNA sequence which comprises a single mismatch represents a diversity of two different DNA sequences within the cell. If the mismatch repair system corrects the mismatch there will only be a diversity of one within the cell.

Alternatively, if the mismatch repair system mediates the degradation of such a duplex DNA sequence the diversity will be lost. See FIG. 1 for a graphic illustration on how the mismatch repair system may work within a cell.

Consequently, if duplex DNA sequences comprising mismatches represent a DNA library of interest, then the diversity of this library may be limited when transformed (placed) into cells with an active mismatch repair system.

The art provides a solution to this problem by making cells wherein the mismatch system is inactive.

EP 449923 describes bacterial cells wherein the mismatch system is inactivated.

WO 97/37011 describes yeast cells wherein the mismatch system is inactivated. See the working examples of this document.

WO 97/05268 describes mice cells wherein the mismatch system is inactivated. See the working examples of this document.

SUMMARY OF THE INVENTION

The problem to be solved by the present invention is to provide an improved strategy for making DNA libraries in filamentous fungal cells. A filamentous fungal cell population comprising such a DNA library may then be used to select a polypeptide of interest. Also polynucleotide sequences with particular properties might be selected, such as promoters, terminators and other regulatory elements with changed/improved properties.

The solution is based on that the present inventors have cloned a novel gene involved in the mismatch repair system of a filamentous fungal cell. Further, this gene is the first gene cloned which is involved in the mismatch repair system of a filamentous fungal cell.

By inactivating this gene in a filamentous cell it is possible to obtain a filamentous cell which is deficient in its mismatch repair system and which is highly useful for preparing DNA libraries in filamentous fungal cells.

The gene comprises a very characterizing DNA sequence encoding the polypeptide sequence shown in positions 683–758 of SEQ ID NO:2.

This DNA has been used to clone the full length gene encoding the polypeptide sequence shown in positions 1–940 of SEQ ID NO:2. See working examples herein (vide infra).

The gene cloned as described in working examples herein is a gene cloned from an *Aspergillus oryzae* filamentous fungal cell.

However, based on the novel sequence information provided herein it is routine work for the skilled person to clone similar homologous genes from other filamentous fungal cells by, e.g., standard hybridization or PCR technology, preferably by using the DNA sequence encoding the polypeptide sequence shown in positions 683–758 of SEQ ID NO:2 as a basis for making a hybridization probe or PCR primers.

Accordingly, in a first aspect the present invention relates to a filamentous fungal cell, wherein a gene involved in the mismatch repair system has been inactivated and in which the gene involved in the mismatch repair system comprises:

(a) a DNA sequence encoding the polypeptide sequence shown in positions 683–758 of SEQ ID NO:2; or (b) a DNA sequence encoding a polypeptide sequence which is at least 70% identical to the polypeptide sequence shown in positions 683–758 of SEQ ID NO:2; and in a second aspect the present invention relates to a filamentous fungal cell, wherein a gene involved in the mismatch repair system has been inactivated and in which the gene involved in the mismatch repair system comprises:

(a) a DNA sequence encoding the polypeptide sequence shown in positions 1–940 of SEQ ID NO:2; or (b) a DNA sequence encoding a polypeptide sequence which is at least 70% identical to the polypeptide sequence shown in positions 1–940 of SEQ ID NO:2.

As stated above a filamentous fungal cell of the first or second aspect of the invention is very suitable for making a DNA library of interest in filamentous fungal cells.

Accordingly, in a third aspect the present invention relates to a process for preparing a filamentous fungal cell population wherein individual cells in the population comprise individually different DNA sequences of interest representing a DNA library of interest comprising the following steps:

(a) placing individually different DNA sequences of interest in a filamentous fungal cell population comprising a filamentous fungal cell of the first or second aspect of the invention; and (b) growing the population of (a) for a period of time allowing an individual DNA sequence of interest in the population to be duplicated at least once under conditions wherein the mismatch repair system gene of the first or second aspect of the invention has been inactivated.

One of the advantages of allowing an individual mismatch repair inactivated filamentous fungal cell duplicated DNA of interest at least once as described under step (b) of the third aspect is illustrated in FIG. 1. As can be seen in FIG. 1 the process of the third aspect using a filamentous fungal mismatch repair inactivated cell as described herein allows preparation of a DNA library wherein eventual hetero duplex DNA mismatches are not corrected. This gives a DNA library with a higher diversity as compared to a DNA library made in a filamentous fungal cell NOT having an inactivated mismatch repair system (see FIG. 1). Duplication of DNA sequence of interest means that the two strands are replicated such that two separate sets of double stranded DNA are generated, each being based on a separate one of the two original strands.

A filamentous fungal cell population wherein individual cells in the population comprise a DNA library of interest as described above may be used to select a polypeptide of interest.

Accordingly, in a fourth aspect the present invention relates to a process for production of a polypeptide of interest comprising the steps of the third aspect and wherein the DNA sequences of interest encode a polypeptide of interest and which further comprises the following step:

(c) selecting from the resultant population of filamentous fungal cells of step (b) of the third aspect a desired polypeptide of interest.

An advantage of the process of the fourth aspect may be that the polypeptide of interest is selected from a filamentous fungal cell expressing the polypeptide. Consequently, it is directly known that the polypeptide can be expressed from a filamentous fungal cell, which is useful if it is subsequently required to produce the polypeptide in large scale in a filamentous fungal cell. This may be of particular interest when the DNA library encodes polypeptides of interest which are derived from filamentous fungal cells, since it is known that filamentous fungal polypeptides preferably are produced in industrial relevant high yields in filamentous fungal cells.

This is contrary to a similar selection process using e.g. a yeast cell. Here the only thing known is that the selected polypeptide is capable of being expressed in yeast and later expression a filamentous fungal cell might give problems, especially if high yields are required.

Definitions

The following section provides definitions of technical features in above-mentioned aspects of the invention.

The term "a gene" denotes herein a gene (a DNA sequence) which is capable of being expressed into a polypeptide within the cell. Accordingly, the gene sequence will be defined as an open reading frame starting from a start codon (normally "ATG", "GTG", or "TTG") and ending at a stop codon (normally "TAA", TAG" or "TGA").

In order to express the gene there must be elements, as known in the art, in connection with the gene, necessary for expression of the gene within the cell. Such standard elements may include a promoter, a ribosomal binding site, a termination sequence, and may be other elements as known in the art.

The term "mismatch repair system" shall herein be understood according to the art, as a system within cells which recognizes mismatches in duplex DNA sequences. (See e.g. WO 97/37011, page 1, line 21–28)

The mismatch repair system then either corrects the mismatches which are seen as errors by e.g. using the methylated "old" strain as template or alternatively it may mediate degradation of the duplex DNA sequences which comprise the mismatches.

Independently on the precise mechanism the end result will be that the "mismatch repair system", will limit the "diversity" within the cell represented by such duplex DNA sequences which comprise mismatches.

For example, a duplex DNA sequence which comprises a single mismatch represents a diversity of two different DNA sequences within the cell. If the mismatch repair system corrects the mismatch their will only be a diversity of one within the cell. Alternatively, if the mismatch repair system mediates the degradation of such a duplex DNA sequence this diversity will be lost.

A polypeptide encoded by a gene involved in the mismatch repair system recognizes a mismatch by a mechanism involving binding to the mismatch.

Accordingly, a suitable assay to test whether or not a filamentous fungal cell as described herein is inactivated in its mismatch repair system is to use a "gel shift assay" or alternatively termed a "gel retardation assay." This is a standard assay used in the art. See WO 97/05268, pages 16, 17 and 25.

The principle in such an assay is that cell extracts are prepared of both (a) a filamentous fungal cell wherein the gene, as described herein, involved in the mismatch repair system is inactivated; and (b) the corresponding filamentous fungal cell wherein the gene is NOT inactivated. These extracts are then bound/mixed to oligonucleotides containing the base-pair mismatched G:T; G:A; G:G; A:C, and an extrahelical TG dinucleotide and run on a nondenaturing gel.

If the gel shift assay demonstrates that the control filamentous fungal cell wherein the gene is NOT inactivated comprises any protein(s) which binds to any of above mentioned oligonucleotides and these binding protein(s) are NOT seen in the filamentous fungal cell wherein the gene, as described herein, involved in the mismatch repair system is inactivated then it is a confirmation that the mismatch repair system in the latter is inactivated.

A detailed description of a suitable gel shift assay is provided in working example 1 herein.

The sequence identity in relation to the phrases

"a DNA sequence encoding a polypeptide sequence which is at least 70% identical to the polypeptide sequence shown in positions 683–758 of SEQ ID NO:2" and "a DNA sequence encoding a polypeptide sequence which is at least 70% identical to the polypeptide sequence shown in positions 1–940 of SEQ ID NO:2";

is determined as the degree of identity between two sequences indicating a derivation of the first sequence from the second. The identity may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for polypeptide sequence comparison: GAP creation penalty of 3.0 and GAP extension penalty of 0.1, the polypeptide encoded by an analogous DNA sequence of the invention exhibits a degree of identity preferably of at least 70%, more preferably at least 80%, more preferably at least 90%, more preferably at least 95%, and especially at least 97% with amino acid sequence shown in positions 683–758 of SEQ ID NO:2, according to the first aspect of the invention; or with amino acid sequence shown in positions 1–940 of SEQ ID NO:2, according to the second aspect of the invention.

The term "DNA library" denotes herein a library of at least two different DNA sequences. For many practical purposes the library is much bigger. Accordingly, the DNA library preferably comprises at least 1000 different DNA sequences, more preferably at least 10000 different DNA sequences, and even more preferably at least 100000 different DNA sequences.

The term "placing individually different DNA sequences of interest in a filamentous fungal cell population" in relation to step (a) in the process of the third aspect of the invention shall herein be understood broadly in the sense that it is NOT identical DNA sequences of interest which are placed in the filamentous fungal cell population. In the present context, relating to a process for making a DNA library using a mismatch repair deficient cell, the term should preferably denote a situation wherein a cell within the filamentous fungal cell population comprises at least two different DNA sequences of interest which are so partially homologous that they are capable of hybridizing/recombining to each other within the cell. It is within the skilled person's general knowledge to determine how partially homologous such sequences have to be in order to obtain said recombination within the cell.

A practical example may be that single stranded oligonucleotide sequences partially homologous to chromosomal DNA sequence are placed within the cell or duplex DNA sequences comprising mismatches (e.g. comprised within a vector) are placed within the cell. See below for further description of such examples.

The specific experimental way of placing these DNA sequences within a filamentous cell may be done according to any of the many suitable techniques, such as transformation techniques.

The phrase "growing the population of (a) for a period of time allowing an individual DNA sequence of interest in the population to be duplicated at least once under conditions wherein the mismatch repair system gene has been inactivated" according to step (b) of the third aspect of the invention denotes that after an individual cell has duplicated itself at least once then the mismatch repair system may be activated again without losing the advantage of the process. The technical reason for this is illustrated in FIG. 1. In this example a duplex DNA sequence comprising a single mismatch is placed in a filamentous cell. After the cell has been duplicated once under conditions wherein the mismatch repair system gene has been inactivated the two individually different single stranded DNA sequences within the duplex DNA have individually been duplicated providing two different duplex sequences, one in each duplicated cell, without any mismatches. Accordingly, since such a cell does NOT comprise duplex DNA sequences of interest having mismatches then there is no technical need for maintaining the mismatch repair system inactivated.

In sections below are described preferred embodiments of the invention by way of examples only.

Figure 1:
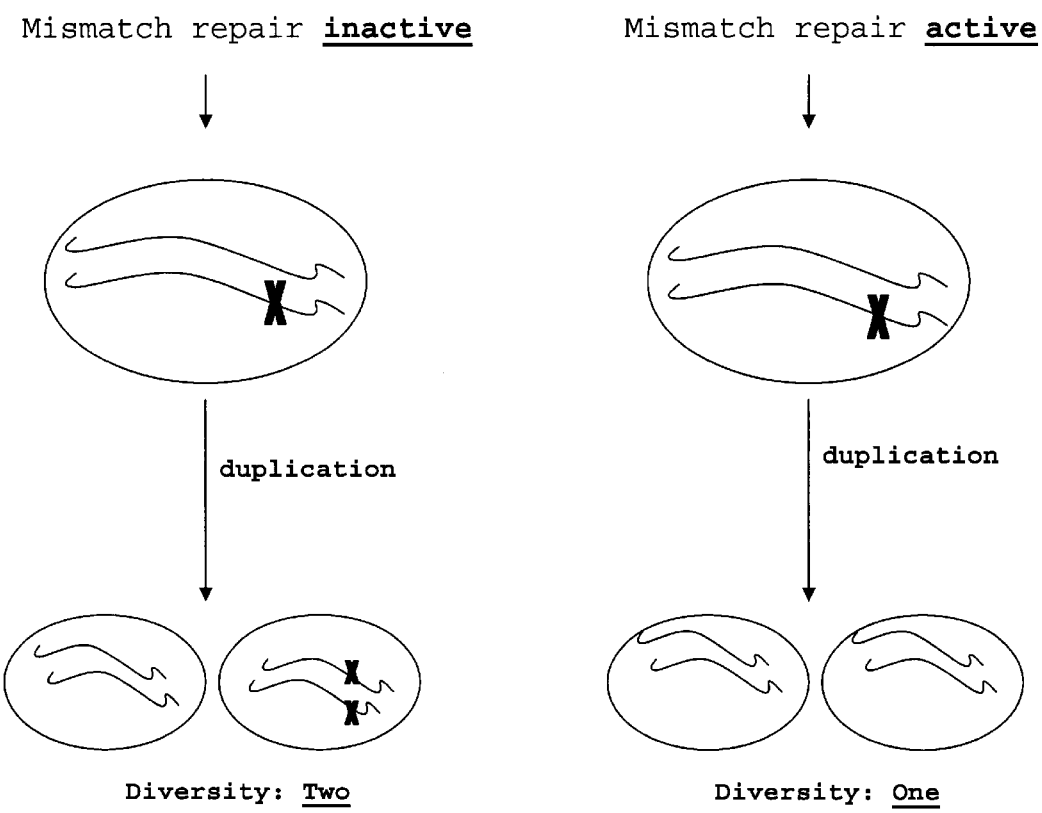
FIG. 1.

This figure illustrates an example wherein a duplex DNA sequence comprising a single mismatch is placed in filamentous cell. After the cell has been duplicated once under conditions wherein the mismatch repair system gene has been inactivated the two individually different single stranded DNA sequences within the duplex DNA have individually been duplicated providing two different duplex sequences, one in each duplicated cell, without any mismatches. On the contrary, in a cell wherein the mismatch repair system is active, a mismatch within a duplex is corrected.

FIG. 2:

This figure shows three partial *Aspergillus oryzae* polypeptide sequences: 'msh2'Ao-col10/13/15 derived from cloned PCR fragments. The three partial polypeptide sequences are aligned with two other partial polypeptide sequences of known mismatch repair proteins: a human mismatch repair protein, msh2-human.p, and a fungal *Saccharomyces cerevisiae* mismatch repair protein, S.c. msh2. The underlined sequences in the figure derive from the construction of the PCR fragments.

FIGS. 3A–3E:

This figure shows an alignment of the proposed polypeptide sequence of the putative *Aspergillus oryzae* mismatch repair protein (Ao.MSH2) with the polypeptide sequences of three known mismatch repair proteins from human (msh2-human.p), mouse (msh2-mus.p), and yeast (S.c. msh2).

DETAILED DESCRIPTION OF THE INVENTION

A Filamentous Fungal Cell, as Described Herein, Wherein a Gene, as Described Herein, Involved in the Mismatch Repair System Has Been Inactivated Inactivation of a Gene Involved in the Mismatch Repair System The novel gene, as described herein, involved in the mismatch repair system may be inactivated by any of the numerous known techniques known to the skilled person.

An embodiment of the invention relates to a filamentous fungal cell as described herein, wherein the gene involved in the mismatch repair is defective.

Numerous methods are known to the skilled person to make a gene defective when the DNA sequence is KNOWN. These methods include deleting part of the DNA sequence of the gene, introducing frame-shift mutations by deleting or inserting nucleotides, introducing stop codons, etc.

A preferred embodiment of the invention relates to a filamentous fungal cell as described herein, wherein the gene involved in the mismatch repair has been inactivated transitorily.

Similarly to above, a number of methods are known to the skilled person for doing this, including insertion of a regulatable promoter upstream of the gene or, e.g., permanently deleting part of the gene on the chromosome followed by inserting a vector (e.g. a plasmid) into the cell which comprises the gene. The plasmid may then comprise a regulatable promoter upsteam of the gene or it may be that the plasmid can be removed from the cell when the mismatch repair system shall be inactivated transitorily and then reinserted into the cell when the mismatch repair system shall be reactivated.

It is within the skilled person's general knowledge to choose the appropriate strategy for a specific technical purpose.

A preferred way to make a filamentous fungal cell which is capable of transitorily inactivating the mismatch repair system as described herein is first to permanently inactive the mismatch repair gene described herein on the chromosome of the cell followed by inserting a plasmid into the cell which comprises the gene, wherein the plasmid comprises a suitable replication initiating sequence and a suitable selectable marker.

Preferably the suitable replication initiating sequence is AMA1 (Gems, D., et al. (1991, Gene 98:61–67).

A more detailed description of suitable replication initiating sequences and suitable selectable markers is provided immediately below, and in working example 4 herein is provided an example of this strategy using a plasmid comprising AMA1 as replication initiating sequence and AmdS as selectable marker.

Replication Initiating Sequences

As used herein, the term "fungal replication initiating sequence" is defined as a nucleic acid sequence which is capable of supporting autonomous replication of an extra-chromosomal molecule, e.g., a plasmid or a DNA vector, in a fungal host cell, normally without structural rearrangement of the plasmid or integration into the host cell genome. The replication initiating sequence may be of any origin as long as it is capable of mediating replication initiating activity in a fungal cell. Preferably, the replication initiating sequence is obtained from a filamentous fungal cell, more preferably a strain of Aspergillus, Fusarium or Alternaria, and even more preferably, a strain of *A. nidulans, A. oryzae, A. niger, F. oxysporum* or *Alternaria altenata*.

A replication initiating sequence may be identified by methods well-known in the art. For instance, the sequence may be identified among genomic fragments derived from the organism in question as a sequence capable of sustaining autonomous replication in yeast, (Ballance and Turner, Gene, 36 (1985), 321–331), an indication of a capability of autonomous replication in filamentous fungal cells. The replication initiating activity in fungi of a given sequence may also be determined by transforming fungi with contemplated plasmid replicators and selecting for colonies having an irregular morphology, indicating loss of a sectorial plasmid which in turn would lead to lack of growth on selective medium when selecting for a gene found on the plasmid (Gems et al, Gene, 98 (1991) 61–67). AMA1 was isolated in this way. An alternative way to isolate a replication initiating sequence is to isolate natural occurring plasmids (e.g. as disclosed by Tsuge et al., Genetics 146 (1997) 111–120 for *Alternaria aternata*).

Examples of replication initiating sequences include, but are not limited to, the ANS1 and AMA1 sequences of *Aspergillus nidulans*, e.g., as described, respectively, by Cullen, D., et al. (1987, Nucleic Acids Res. 15:9163–9175) and Gems, D., et al. (1991, Gene 98:61–67).

The term "replication initiating activity" is used herein in its conventional meaning, i.e. to indicate that the sequence is capable of supporting autonomous replication of an extra-chromosomal molecule, such as a plasmid or a DNA vector in a fungal cell.

The term "without structural rearrangement of the plasmid" is used herein to mean that no part of the plasmid is deleted or inserted into another part of the plasmid, nor is any host genomic DNA inserted into the plasmid.

Filamentous Fungal Selective Marker

The term "selective pressure" is defined herein as culturing a filamentous fungal cell, containing a DNA vector containing a fungal selective marker gene operably linked to a polynucleotide sequence of interest, in the presence of an effective amount or the absence of an appropriate selective agent. The effective amount of the selective agent is defined herein as an amount sufficient for allowing the selection of cells containing the selection marker from cells which do not contain the selection marker.

In a preferred embodiment, the fungal selective marker is selected from the group of genes which encodes a product capable of providing resistance to biocide or viral toxicity, resistance to heavy metal toxicity, or prototrophy to auxotrophs.

In a more preferred embodiment, the prototrophy is obtained from an enzyme selected from the group of metabolic pathways consisting of nucleotide synthesis, cofactor synthesis, amino acid synthesis, acetamide metabolism, proline metabolism, sulfate metabolism, and nitrate metabolism.

In an even more preferred embodiment, in the methods of the present invention the fungal selective marker is a gene selected from the group consisting of argB (ornithine carbamoyltransferase), amdS (acetamidase), bar (phosphinothricin acetyltransferase), hemA (5-aminolevulinate synthase), hemB (porphobilinogen synthase), hygB (hygromycin phosphotransferase), niaD (nitrate reductase), prn (proline permease), pyrG (orotidine-5'-phosphate decarboxylase), pyroA, riboB, sC (sulfate adenyltransferase), and trpC (anthranilate synthase).

The fungal cell is cultivated in a suitable medium and under suitable conditions for screening or selecting for transformants harboring the variant polynucleotide sequence of interest having or encoding the desired characteristic. The cultivation may be performed in accordance with methods well-known in the art for screening of polynucleotide variant libraries.

The Filamentous Fungal Cell

The filamentous fungal cell as described herein includes all filamentous forms of the subdivision Eumycota and Oomycota. The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a preferred embodiment, the filamentous fungal cell is a cell of a species of, but is not limited to, Acremonium, Aspergillus, Fusarium, Humicola, Mucor, Myceliophthora, Neurospora, Penicillium, Scytalidium, Thielavia, Tolypocladium, and Trichoderma.

Examples of filamentous fungal cells of use in the present invention include an Aspergillus cell, an Acremonium cell, a Fusarium cell, a Humicola cell, a Mucor cell, a Myceliophthora cell, a Neurospora cell, a Penicillium cell, a Thielavia cell, a Tolypocladium cell, and a Trichoderma cell.

More specifically, the filamentous fungal cell is an *Aspergillus awamori, Aspergillus foetidus, Aspergillus japonicus, Aspergillus nidulans, Aspergillus niger*, or *Aspergillus oryzae* cell;

a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotricioides, Fusarium sulphureum, Fusarium torulosum, Fusarium trichothecioides, Fusarium venenatum* cell or a *Fusarium venenatum* cell (Nirenberg sp. nov; a *Humicola insolens* cell or a *Humicola lanuginosa* cell; a *Mucor miehei* cell; a *Myceliophthora thermophila* cell; a *Neurospora crassa* cell; a *Penicillium purpurogenum* cell; a *Thielavia terrestris* cell; or a *Trichoderma harzianum, Trichoderma koningii, Trichoderma longibrachiatum, Trichoderma reesei*, or *Trichoderma viride* cell.

A Process for Preparing a Filamentous Fungal Cell Population Comprising a DNA Library According to the Third Aspect of the Invention Placing Individually Different DNA Sequences of Interest in a Filamentous Fungal Cell Population According to Step (a) of the Process of the Third Aspect of the Invention As stated above, the specific experimental way of placing these DNA sequences within a filamentous cell may be done according to any of the many suitable techniques, such as transformation techniques. See the general fungal textbook "Fungal Genetic" (1996, ISBN 0-8247-9544-X) for a further description of such standard techniques.

A practical example may be that single stranded oligonucleotide sequences partially homologous to chromosomal DNA sequence are placed within the cell. See Calissano et al., Fungal genetic newsletter 43:15–16 (1995) for further description of this.

Another example may be that duplex DNA sequences comprising mismatches (e.g. comprised within a vector as shown in FIG. 1) are placed within the cell.

In an preferred embodiment the different DNA sequences of interest are comprised in a plasmid wherein the plasmid comprises a suitable replication initiating sequence and a suitable selectable marker as described above.

Preferably the suitable replication initiating sequence is AMA1 (Gems, D., et al. (1991, Gene 98:61–67).

Growing the Population of Step (a) for a Period of Time Allowing an Individual DNA Sequence of Interest in the Population to be Duplicated at Least Once Under Conditions Wherein the Mismatch Repair System Gene, as Described Herein Has Been Inactivated, According to Step (b) of the Third Aspect of the Invention Growing of the population may be done in any of the numerous suitable known media for growing filamentous fungal cells. It is within the skilled person's general knowledge to choose such a suitable media.

As explained above an individual cell in the population must be allowed to be duplicated at least once under conditions wherein the mismatch repair system gene, as described herein, has been inactivated.

The cells may, of course, be allowed to be duplicated more than once under conditions wherein the mismatch repair system gene has been inactivated.

Since inactivation of the mismatch repair system normally will cause accumulation of mutations on the chromosomal DNA within the cell, and thereby maybe make lethal mutations to the cell, the actual preferred number of duplication cycles as described above will depend on how fast such potential lethal mutations arise.

It is within the skilled person's general knowledge to determine how many duplication cycles it preferred.

Due to these potential lethal mutations it is preferred that the mismatch repair system under step (b) be inactivated transitorily.

After suitable cycles of duplication according to step (b) of the third aspect the transitorily inactivated mismatch repair system the mismatch repair system is then re-activated in order to avoid these lethal mutations in the filamentous fungal cell as such. The strategy for this transitory inactivation may be any of the strategies described above.

Another strategy to limit introduction of mutations on the chromosome, is to transitorily stop the chromosomal replication while replicating the extrachromosomal element under mismatch repair deficient conditions. This can be achieved by introducing mutations in elements being solely necessary for the chromosomal replication.

A preferred strategy is to use a filamentous fungal cell wherein the gene involved in the mismatch repair system as described herein is permanently inactivated on the chromosome of the cell followed by inserting a plasmid into the cell which comprises the gene, wherein the plasmid comprises a suitable replication initiating sequence and a suitable selectable marker. See above for a further explanation of this strategy.

Preferably the suitable replication initiating sequence is AMA1 (Gems, D., et al. (1991, Gene 98:61–67).

A further embodiment relates to the process of the third aspect of the invention, wherein the mismatch repair system under step (b) is defective.

In a further embodiment the invention relates to a process as described herein, wherein, under step (b) of the third aspect of the invention, there is an in vivo intergenic recombination of partially homologous DNA sequences of interest.

Since the overall concept of the present invention is to provide a process involving inactivation of the mismatch system it is of course preferable that the partially homologous DNA sequences are capable of in vivo forming duplex DNA sequences comprising mismatches.

A Process for Production of a Polypeptide of Interest Comprising the Steps of the Third Aspect of the Invention and Wherein the DNA Sequences of Interest Encode a Polypeptide of Interest, According to the Fourth Aspect of the Invention Selecting from the Resultant Population of Filamentous Fungal Cells of Step (b) of the Third Aspect a Desired Polypeptide of Interest, According to Step (c) of the Fourth Aspect The desired polypeptide of interest may be any polypeptide comprising a desired technical feature, such as improved stability, a desired specific activity, a desired pH optimum, an improved wash performance in a detergent, etc.

The specific strategy for selecting this desired polypeptide of interest may be any of the numerous selecting strategies known to the skilled person, such as plate screening assays, micro-titer plate based assays, etc.

An embodiment of the invention relates to a process of the fourth aspect of the invention, which further comprises the following steps:

(d) an optional step comprising modifying the amino acid sequence of the desired selected polypeptide of interest according to a particularly further specific need;

(e) placing the DNA sequence encoding the polypeptide of interest of step (c) of the fourth aspect or the modified polypeptide of interest of step (d) into a filamentous fungal cell which is suitable for large scale production of the polypeptide of interest;

(f) cultivating the filamentous fungal cell of step (e) in a fermentor of at least 10000 m3 under conditions permitting expression of the polypeptide of interest; and (g) isolating the polypeptide of interest.

This embodiment relates to an industrial, very relevant process, wherein the selected polypeptide of interest is produced in large scale.

The optional step (d) relates to a situation wherein, e.g., the desired polypeptide of interest is selected in order to, e.g., identify a polypeptide with improved wash performance in a detergent according to step (c) of the third aspect of the invention. This polypeptide while having improved wash performance in a detergent may not be sufficiently stable for a commercial product. Accordingly, it may be required to make some further amino acid substitutions in this selected polypeptide, such as e.g. suitable Proline substitutions in order to obtain sufficient stability to commercializing this polypeptide.

A further embodiment relates to a process of the embodiment immediately above, wherein the filamentous fungal cell which is suitable for large-scale production of the polypeptide of interest of step (e) the embodiment is another filamentous fungal cell as compared to the filamentous fungal cell of step (a) of the third aspect of the invention.

This embodiment relates to a situation wherein the filamentous fungal cell used to select the polypeptide of interest is different from the one which is used for large scale production.

A further embodiment relates to a process as described herein, wherein the polypeptide of interest is a polypeptide derived from a filamentous fungal cell.

The phrase "derived from a filamentous fungal cell" should be understood in the sense that the information in the amino acid sequence of the polypeptide of interest is derived from a polypeptide obtained from a filamentous fungal cell.

Consequently, it may be a variant of a wild-type filamentous fungal polypeptide and/or may be a polypeptide which is a result of a recombination/shuffling of two or more different filamentous fungal polypeptides.

In an even further embodiment the invention relates to a process as described herein, wherein the polypeptide of interest is an enzyme, such as an amylase, a protease, a cellulase, a lipase, a xylanase or a phospholipase.

EXAMPLES

Materials

Chemicals used as buffers and substrates were commercial products of at least reagent grade.

Example 1

A Gel Shift Assay Suitable for Determining if a Filamentous Fungal Cell as Described Herein is Inactivated in the Mismatch Repair System The principle in this gel shift assay is that cell extracts are prepared of both (a) a filamentous fungal cell wherein the gene, as described herein, involved in the mismatch repair system is inactivated; and (b) the corresponding filamentous fungal cell wherein the gene is NOT inactivated. These extracts are then bound/mixed to oligonucleotides containing the base-pair mismatched G:T; G:A; G:G; A:C, and an extrahelical TG dinucleotide and run on a nondenaturing gel.

If the gel shift assay demonstrates that the control filamentous fungal cell wherein the gene is NOT inactivated comprises any protein(s) which binds to any of above mentioned oligonucleotides and these binding protein(s) is NOT seen in the filamentous fungal cell wherein the gene, as described herein, involved in the mismatch repair system is inactivated then it is a confirmation that the mismatch repair system in the latter is inactivated.

Experimental Procedure

Preparation of cell extracts are performed as described in Nagata et al. (Mol. Gen Genet (1993) 237:251–260; See Materials and Methods).

Annealing of oligonucleotides, binding of cell extracts to duplex oligonucleotides containing mismatched, and nondenaturing polyacrylamide gel electrophoresis are performed essentially as described (Stephenson and Karran; Selective binding to DNA base pair mismatches by proteins from human cells; J. Biol. Chem. 264:2177–21182 (1989)).

However, gel electrophoresis is performed in TAE buffer rather than in TBE buffer. To obtain duplex oligonucleotides, the oligonucleotide U is radiolabelled and annealed with any of the unlabelled oligonucleotides L-G.T, L-G.A, L-G.C, L-A.C, L-T.G., or L-HOM. Oligonucleotide sequences are derived from Aquilina et al. Proc. Natl. Acad. Sci. USA 91:8905–8909 (1994).

U:
5'-GGGAAGCTGCCAGGCCCCAGTGTCAGCCTCCTATGCTC-3' (SEQ ID NO: 3);

L-G.T:
5'-GAGCATAGGAGGCTGACATTGGGGCCTGGCAGCTTCCC-3' (SEQ ID NO: 4) (resulting in a G.T mismatch);

L-G.A.:
5'-GAGCATAGGAGGCTGACAATGGGGCCTGGCAGCTTCCC-3' (SEQ ID NO:5) (resulting in a G.A mismatch);

L-G.G.:
5'-GAGCATAGGAGGCTGACAGTGGGGCCTGGCAGCTTCCC-3' (SEQ ID NO:6) (resulting in a G.G mismatch);

L-A.C.:
5'-GAGCATAGGAGGCTGACACCGGGGCCTGGCAGCTTCCC-3' (SEQ ID NO:7) (resulting in a A.C mismatch);

L-TG:
5'-GAGCATAGGAGGCTGACACTGTGGGGCCTGGCAGCTTCCC-3' (SEQ ID NO:8) (resulting in an extrahelical TG dinucleotide);

L-HOM:
5'-GAGCATAGGAGGCTGACACCGGGGCCTGGCAGCTTCCC-3' (SEQ ID NO: 9) (resulting in a homoduplex).

In all assays, a twofold excess of unlabelled homoduplex competitor oligonucleotide is included.

Example 2

Cloning of a Gene Involved in the Mismatch Repair System of an *Aspergillus oryzae* Cell The gene cloned as described in this example is shown in SEQ ID NO:1 (DNA sequence) and SEQ ID NO:2 (the translated amino acid sequence).

Several sequences of mismatch repair proteins from various organisms are known, only three of these have been utilized in the following: *S. cerevisiae* (M84170), *H. sapiens* (L47580) and mouse (U21011).

The numbers indicated are reference numbers from the public available GenBank database.

Based on the C-terminal homology between known mismatch repair proteins, a set of degenerate primers were designed, aiming at amplification of a partial sequence of the *Aspergillus oryzae* homolog:

Pr 117858 (SEQ ID NO:10):
P-GGCNCARATHGGNTGYTTYGTNCC

Pr 117859 (SEQ ID NO:11):
P-GCCCANGCNARNCCRAANCC

With chromosomal DNA from *A. oryzae* strain JaL142 (WO 96/29391) as template, and above primers the following 50 µl PWO polymerase based PCR reaction was performed at eight $MgSO_4$ concentrations (0.5 mM to 4.0 mM, as recommended by the manufacturer; Boehringer M.). 1 mM $MgSO_4$ was found to be optimal and gave a discrete band of appr. 230 bp as would be expected if no introns were embodied in the sequence.

PCR-cycle profile: [96° C.; 2 min-30 cycles of (94° C.; 15 s-50° C.; 15 s-72° C.; 30 s)-72° C., 7 min-4° C.; hold].

The 230 bp PCR fragment was blunt end ligated into filled in BamH1 site of pUC19. pUC19 was BamH1 cleaved in presence of calf intestine alkaline phosphatase, followed by filling in the sticky ends by klenow polymerase and dNTP. Three individual plasmids harboring the insert were isolated from *E.coli* XL1 transformants of above ligation, and sequenced. Alignment of polypeptides derived by translation of the cloned PCR fragments, revealed a strong homolgy to known mismatch repair protein sequences (see FIG. 2).

The underlined sequences of FIG. 2 are sequences derived from the consensus PCR primers described above.

The three Aspergillus sequences of FIG. 2 are equal to the sequence shown in SEQ ID NO:2 from positions 683–758, except from position 685 which in the final cloned sequence is a Thr (T) instead of an Ile (I) as indicated above. This is due to the sequence in above mentioned consensus primers.

The alignment shown in FIG. 2 clearly demonstrates that the cloned fragment originates from an *A. oryzae* homologue of a mismatch repair protein.

To clone the entire gene, a radiolabeled probe of the cloned fragment was generated by PCR, using 0.5 mg pUC19'msh2'-13 (see above) as template in a 100 ml reaction with Taq polymerase, 30 pmol pUC forward and reverse primers and 0.2 mM of dG-, dC-, dTTP and 0.2 mM dATP+$^{32}$P-dATP. The generated radiolabeled probe was liberated from pUC19 sequences by EcoR1-Hind3 digestion followed by gel purification of the resulting 293 bp fragment.

The probe was hybridized to a membrane gridded cosmid library of genomic DNA from *A. oryzae* strain A1560 (the father of JaL142) (WO96/29391). A positive clone was identified on the filter when analyzed in a phosphoimager, and the clone was identified as λ31A2.

The λ31A2 cosmid DNA was propagated and used for southern analysis, using the same radiolabeled primer as above. An approximately 9 Kb Pst fragment, split by BstX (previously found in the cloned PCR fragment) into 5.8 and 3.2 kb fragments both lightening up with the probe, was identified and cloned into Pst cut pUC19, giving a plasmid named pUC19msh2P. The insert was sequentially sequenced, starting with primers pointing out from the previously determined sequence, followed by primers based on the sequences determined in the last run:

130740 (SEQ ID NO:12): GCTCGAAACATCCAACATCC
130741 (SEQ ID NO:13): GCTGTGAATCACTTGCACC
131928 (SEQ ID NO:14): CTTCATAAACTGCGACAAAT-CATGC
131929 (SEQ ID NO:15): GGAGGAGCATCTTCGC
131930 (SEQ ID NO:16): GGAACTTGAAGACTTTACT-TCATCC
134608 (SEQ ID NO:17): CCAGAAACTCGCTAACACC
134609 (SEQ ID NO:18): GTGCTTTGCGGACGC
134610 (SEQ ID NO:19): CAGGACAGTAGGACGC
135320 (SEQ ID NO:20): CGAGCGATGAACTCTGC
135321 (SEQ ID NO:21): GCGTTGGTGGATTATCC
136105 (SEQ ID NO:22): CGTTGCATCTATCATATACC
136106 (SEQ ID NO:23): GGTATATGATAGATG-CAACGC

The 3825 bp sequence hereby determined (SEQ ID NO:1) was translated in the frame previously determined in the PCR fragment. The resulting protein (SEQ ID NO:2) called Ao.MSH2 was aligned to the protein sequences of known mismatch repair proteins in FIG. 3. From the alignment shown in FIG. 3 the cloned and sequenced DNA clearly encompasses the coding sequence for a homolog of yeast, man and mouse mismatch repair proteins, with one intron in the N-terminal part. The position of the intron was deduced by the standard splice rules, and constitutes the only possibility.

Example 3
Disruption of the Gene Cloned in Example 1 on the Chromosome of an *Aspergillus oryzae* Cell For the disruption experiment the msh2 CDS was deleted from pUC19msh2P (see example 2) by PCR, introducing a NotI site instead. This was done by the primers:
137208 (SEQ ID NO:24): 5' P-CCGCGTCTCCAACAAGATGAATGG
137207 (SEQ ID NO:25): 5' P-CCGCTTTCTCGGGGTCATAGC In a Pwo polymerase based PCR reaction with 2.5 mM MgSO$_4$ and 50 pg pUC19msh2P (conditions according to the manufacturer):

PCR-cycle profile: [96° C.; 2 min-4 cycles of (94° C.; 30 s -52° C.; 30 s-72° C.; 3 min)-25 cycles of (94° C.; 30 s-59° C.; 30 s-72° C.; 3 min)-72° C.; 10 min]

The resulting PCR product of appr. 8.9 Kb was isolated, ligated into pUC19, and transformed into *E. coli* XL1. From the resulting transformants pMsh2Δ was isolated, and the correctness of the new junction and its surroundings verified by sequencing [primer 138149 (SEQ ID NO:26): CCTTTCCACTTTAATCCTAAGC]. (X11/pMsh2Δ: Lac3073).

In this construct it the *A.oryzae* pyrG (WO 96/29391) is inserted into the NotI site.

By using this construct the chromosomal gene is deleted in an *Aspergillus oryzae* cell according to standard techniques known in the art for crossing in such a deleted gene on the chromosome by homologous recombination (Miller, B. L., et al., 1985 Mol. and Cell. Biol. 5:1714–1721).

Example 4
Construction of a Plasmid Comprising the Mismatch Repair Gene Shown in SEQ ID NO:1, the AMA1 Replication Initiating Sequence, and the AmdS Selectable Marker The plasmid constructed as described below is highly suitable for making a filamentous fungal cell wherein the mismatch repair system may be transitorily inactivated, wherein this plasmid may be inserted into a mismatch disrupted strain of example 3 when the mismatch repair system shall be activated and deleted from the strain when the mismatch repair system shall be inactivated.

Disruption of the mismatch repair gene may cause the accumulation of new chromosomal mutations, thus such a strain might be genetically unstable. Consequently it was decided to perform the chromosomal disruption in a strain where mismatch repair gene was expressed from an extra chromosomal element readily lost when the Δmismatch repair phenotype was wanted.

The extrachromosomal element was here a plasmid comprising AMA1 as replication initiating sequence and AmdS as selectable marker.

For this purpose the mismatch repair gene (SEQ ID NO:1) was cloned into an autonomously replicating construct harbouring one AMA1 repeat.

From pMT1505 (See example 5 below for description of pMT1505) the following fragments were isolated and ligated together:

5.16 kb NotI-[Hind3]*+3.515 kb [Sal]*-BamH1+757 bp BamH1-NotI

[ ]* indicates that the site has been filled in by Klenow-polymerase and dNTP

From this ligation reaction pMT1505DHS was isolated (LaC 3212), and the mismatch repair expression cassette was introduced as a BamH1-Mun1 fragment in the corresponding sites in pMT1505DHS, resulting in the plasmid pAma-msh2 (LaC 3216).

*Aspergillus oryzae* JaL250 (see example 5) was transformed AmdS$^+$ with pAma-msh2, and the transformants checked for the ability to lose the amdS character when unselected (50% of the transformants), indicating the maintanance of this plasmid as extrachromosomal. (LaC3244 keep on acetamide+uridine).

Example 5
Construction of Plasmid pMT1505 Used in Example 4
Plasmids
pMT1505: constructed as described below in Example 5
pHelp1: contains the pyrG gene from *A. oryzae* as a selective marker and the AMA1 sequences which enable autonomous replication in *A. nidulans* as described by Gems, D., et al. (1991. Gene 98: 61–67)
pToC68: as described in EP 0 531 372 (Novo Nordisk A/S)

Strains

JaL250: a derivative of *Aspergillus oryzae* A1560 in which the pyrG gene has been inactivated, as described in WO 98/01470

DH5a: an *E. coli* host cell purchased from GIBCO BRL (Life Technologies, Inc., Rockville Md.)

pMT1466 was constructed by inserting an SphI/NarI fragment from pHelp1 into pToC68. pMT1489 was constructed by digesting pMT1466 with SphI and StuI, then religating. pMT1500 was constructed by digesting pMT1489 with AatII and NarI and ligating a linker. pMT1504 was constructed by digesting pMT1500 with NheI and religating.

pMT1505 was constructed by inserting a 2.7 kb XbaI fragment containing the AmdS encoding gene from *A. nidulans* genomic DNA (Corrick, C. M., et al. 1987, Gene 53:63–71) into pMT1504 which had been cut with NheI.

Example 6

Deletion of Part of the mshII Gene on the Chromosome

The plasmid p418MsHII (from lac3159) is cut with SalI and XhoI and treated with calf-intestinal phosphatase. In this manner part of the msHII gene is cut out. The large band (6400 bp) containing the vector and most of the msHII gene is isolated from a 1% agarose gel.

The plasmid pJal554 was constructed by ligating a SpeI/SspBI cut fragment (5330 bp) from pSO2 with a Asp718/NheI cut fragment (316 bp) from pSO2. Plasmid pJal554 is cut with SalI and a 2350 bp band which contains the pyrG gene is isolated on a 1% agarose gel. The 2350 bp band with pyrG is ligated with the cut p418MsHII plasmid and transformed into *E. coli*. The right *E. coli* transformant is identified by restriction analysis and a plasmid preparation is made from this transformant.

The plasmid thus prepared is cut with EcoRI in order to linearize the plasmid before it is transformed into for example *Aspergillus oryzae* Jal250. Transformants are selected on minimal plates.

A transformant where a double crossover event has taken place is identified by making an Aspergillus chromosomal DNA prep followed by a PCR screen for full-length mshII gene using appropriate primers. A Southern blot is made using chromosomal DNA which is randomly fragmented with appropriate enzymes as well as appropriate probes for the deleted msHII fragment (which is not there any longer) as well as a positive control probe.

In order to determine an increased mutation frequency in the strain with an inactivated msHII gene, a screen for mutations in the niaD gene is made. This is done by growing the parent strain Aspergillus Jal250 and the msHII inactivated strain on plates.

A spore-suspension is made and aliquots of spores are plated on a chlorate-containing plate as described by Unkles et al. (S. E. Unkles, E. C. Campbell. Y. M. J. T. de Ruite Jacobs, M. Broekhuisen, J. A. Macro, D. Carrez, R. Contreras, C. A. M. J. J. van den Hondel J. R. Kinghorn. The development of a homologous transformation system for *Aspergillus oryzae* based on nitrate assimilation pathway: A convenient and general selection system for filamentous fungal transformation. Molecular and general genetics V:218 p 99–104 (1989)).

The strain with no expression of the MsHII protein will have a higher rate of niaD mutations (more chlorate resistant clones), than the control strain.

Example 7

Making In Vivo Antisense msHII RNA to Inhibit Translation of msHII mRNA using the TAKA Promoter to Drive Transcription of the Anti-sense mRNA Anti-sense RNA expression is a well-known way to down regulate expression of any gene in vivo (The design of Antisense RNA, Georg Sczakiel, Antisense and nucleic acid drug development V. 7 P. 439–444 (1997))

A pcr fragment is made using the oligo's:

000120j2 (SEQ ID NO:27): TCTGCGAATCGCTTG-GATCCCGAACGCGACAACA C,

000120j4 (SEQ ID NO:28): GAGCTCAGATCTCTTAGGTTCTGGACGAGAAGA, and pUC19msh2P as template. This PCR fragment contains the 5' end of the msHII gene including the presumed part of 5' msHII mRNA. Another PCR fragment is made using the oligo's:

000120j3 (SEQ ID NO:29): GTTGTCGCGTTCGGGATC-CAAGCGATTCGCAGAA G,

1298-TAKA (SEQ ID NO:30): GCAAGCGCGCGCAATACATGGTGTTTTGATCAT, and pENI1298 as template (PCT DK99/00552). Both PCR reactions are done using PWO polymerase according to the manufacturers manual (Boehringer-Mannheim).

The PCR fragments are purified using the Qiagen PCR purification kit (Qiagen). The two PCR fragments are mixed and a third PCR reaction is done with primer 1298-TAKA and 000120j4. In this manner the two PCR fragments are assembled.

The assembled PCR fragment is cut with BssHII and BglII, and purified from a 1.5% agarose gel and ligated with pENI1298 which was cut with BssHII and Bgl II (purified from 1% agarose gel). The ligation mixture is transformed into *E. coli*. A DNA-prep is made of each of the resulting *E. coli* transformants. The assembled PCR fragment is sequenced to confirm that no unwanted mutations are introduced during the procedure. The correct construct contains the TAKA promoter, which drives the transcription of the msHII anti-sense mRNA.

The resulting plasmid is transformed into for example *Aspergillus oryzae* Jal250 along with pENI1298 as control, and transformant are selected on minimal plates. The resulting transformants are isolated on minimal plates and incubated at 37° C. until they sporulate.

To determine an increased mutation frequency in the strain, where the translation of the msHII mRNA is impeded due to msHII anti-sense RNA expression, a screen for mutations in the niaD gene is made. A spore-suspension is prepared of the control transformants (pENi1298) and of the msHII Anti-sense RNA transformants, and equal amounts of spores are plated on to a chlorate-containing plate as described by Unkles et al. (S. E. Unkles, E. C. Campbell. Y. M. J. T. de Ruite Jacobs, M. Broekhuisen, J. A. Macro, D. Carrez, R. Contreras, C. A. M. J. J. van den Hondel J. R. Kinghorn. The development of a homologous transformation system for *Aspergillus oryzae* based on nitrate assimilation pathway: A convenient and general selection system for filamentous fungal transformation. Molecular and general genetics V:218 p 99–104 (1989)).

The strain with no or low expression of the MsHII protein will have a higher rate of niaD mutations (more chlorate resistant clones), than the control strain.

What is claimed is:

1. A filamentous fungal cell, wherein a gene involved in the mismatch repair system has been inactivated and in which the gene involved in the mismatch repair system comprises a DNA sequence encoding the polypeptide sequence shown in positions 683–758 of SEQ ID NO:2.

2. A filamentous fungal cell, wherein a gene involved in the mismatch repair system has been inactivated and in which the gene involved in the mismatch repair system comprises a DNA sequence encoding the polypeptide sequence shown in positions 1–940 of SEQ ID NO:2.

3. The filamentous fungal cell of claims 1 or 2, wherein the gene involved in the mismatch repair is defective.

4. The filamentous fungal cell of claims 1 or 2, wherein the gene involved in the mismatch repair has been inactivated transitorily.

5. The filamentous fungal cell of claims 1 or 2, wherein the filamentous fungal cell is a strain of Fusarium.

6. The filamentous fungal cell of claims 1 or 2, wherein the filamentous fungal cell is a strain of Aspergillus.

7. A process for preparing a filamentous fungal cell population wherein individual cells in the population comprise individually different DNA sequences of interest representing a DNA library of interest, the process comprising the following steps:
   (a) placing individually different DNA sequences of interest in a filamentous fungal cell population comprising a filamentous fungal cell of claims 1 or 2, and
   (b) growing the population of (a) for a period of time allowing an individual DNA sequence of interest in the population to be duplicated at least once under conditions wherein the mismatch repair system gene of claims 1 or 2 has been inactivated.

8. A process for production of a polypeptide of interest comprising:
   (a) placing individually different DNA sequences of interest in a filamentous fungal cell population comprising a filamentous fungal cell of claims 1 or 2, wherein the DNA sequences of interest encode a polypeptide of interest;
   (b) growing the population of (a) for a period of time allowing an individual DNA sequence of interest in the population to be duplicated at least once under conditions wherein the mismatch repair system gene of claims 1 or 2 has been inactivated; and
   (c) selecting from the resultant population of filamentous fungal cells of step (b) a desired polypeptide of interest.

9. A process for production of a polypeptide of interest, comprising:
   (a) placing a DNA sequence encoding a polypeptide of interest into the filamentous fungal cell of claims 1 or 2,
   (b) cultivating the filamentous fungal cell of said (a) for a period of time allowing the DNA sequence encoding the polypeptide of interest to be duplicated at least once under conditions wherein the mismatch repair system gene has been inactivated;
   (c) isolating the polypeptide of interest.

10. The process of claim 7, wherein the mismatch repair system gene under step (b) is defective.

11. the process of claim 7, wherein the mismatch repair system gene under step (b) has been inactivated transitorily.

12. The process of claim 7, wherein the filamentous fungal cell is a strain of Fusarium.

13. The process of claim 7, wherein the filamentous fungal cell is a strain of Aspergillus.

14. The process of claim 7, further comprising the step of recombining homologous DNA sequences of interest.

15. The process of claim 8, which further comprises the following steps:
   (d) placing the DNA sequence encoding the polypeptide of interest of step (c) of claim 13 or the modified polypeptide of interest of step (d) into a filamentous fungal cell, which is suitable for large scale production of the polypeptide of interest;
   (e) cultivating the filamentous fungal cell of step (a) in a fermentor of at least 10000 m3 under conditions permitting expression of the polypeptide of interest; and
   (f) isolating the polypeptide of interest.

16. The process of claim 8, wherein the polypeptide of interest is a polypeptide derived from a filamentous fungal cell.

17. The process of claim 8, wherein the polypeptide of interest is an enzyme selected from an amylase, a protease, a cellulase, a lipase, a xylanase and a phospholipase.

18. The process of claim 15, wherein the filamentous fungal cell which is suitable for large scale production of the polypeptide of interest of step (d) of claim 14 is another filamentous fungal cell as compared to the filamentous fungal cell of step (a) of claim 13.

* * * * *

SEQUENCE LISTING

<160> NUMBER OF SEQ ID NOS: 33

<210> SEQ ID NO 1
<211> LENGTH: 3823
<212> TYPE: DNA
<213> ORGANISM: Aspergillus oryzae
<220> FEATURE:
<221> NAME/KEY: CDS
<222> LOCATION: (700)..(723)
<223> OTHER INFORMATION:
<220> FEATURE:
<221> NAME/KEY: CDS
<222> LOCATION: (781)..(3576)
<223> OTHER INFORMATION:
<220> FEATURE:
<221> NAME/KEY: Intron
<222> LOCATION: (724)..(780)
<223> OTHER INFORMATION:

<400> SEQUENCE: 1

```
gtgggtagtg gcccaaaagc tactgtggct gcccagagga agccgtttcg cctagagatg      60
atcgtacaga acgttcagga ctcatcgaag aatcctattt cagagaaaga ggtggaaatc     120
tgcgtcgaag tgctggctcg gcccgacatt gctggacaat gggtcgattt cgtcaccgtg     180
aatcatatca aatcggtggt tctgaaatcc tccgcggata tcaacctcaa ggatatcggt     240
gcgaaggtgc gtgaactgaa gttcggcgag gacgagcctg cttcagcctc gaacccctaa     300
tcaagacttc tactgtttaa tgtgtgtttt ggatgtttgg tgttgctggg ttggataccc     360
catctgtgga gtttgataca catgacttta ttatcaccct tgtgtagcat ctgttagcgt     420
tgcatctatc ataccatt ttagctatta gagaatacat atcaatcatg atgaacatga      480
agtacttcag ttcctatgtg taggcgtttt ttggacctat cactttgtag agttctaacg     540
ggtgctatta ttggccaatg atacttcaat atatcgcgaa cgcgacaaca cgtgaccgcg     600
ttgccacgga gcgcgtctcc tggaattatc gaaatagatc gatcacggca gagctaatgg     660
tcagtcttcc attcatcttg ttggagacta actggcaag  atg tct tct cgt cca       714
                                             Met Ser Ser Arg Pro
                                              1               5 gaa ctt aag  gtaagtaaac aagacaaccg gtctctcgaa cattcaataa                 763
Glu Leu Lys caattaaccc tgtttag  gtt gac gac gaa gtc ggc ttc att cgt ttt tac         813
                    Val Asp Asp Glu Val Gly Phe Ile Arg Phe Tyr
                             10                  15 cgt tcc ctc gca gca aat agc aac gat gaa act att cgc gtt ttc gac         861
Arg Ser Leu Ala Ala Asn Ser Asn Asp Glu Thr Ile Arg Val Phe Asp
 20                  25                  30                  35 cgc ggt gac tgg tac tct gcc cat ggc gcc aaa gca gag ttc atc gct         909
Arg Gly Asp Trp Tyr Ser Ala His Gly Ala Lys Ala Glu Phe Ile Ala
                 40                  45                  50 cgc act gtg tac aag acc acc tct ata ctc cgc aat cta ggt cgc agc         957
Arg Thr Val Tyr Lys Thr Thr Ser Ile Leu Arg Asn Leu Gly Arg Ser
             55                  60                  65 gac tca gga ggc ctt ccc tcc gtc acc atg agt gtc acc gtc ttc cgt        1005
Asp Ser Gly Gly Leu Pro Ser Val Thr Met Ser Val Thr Val Phe Arg
         70                  75                  80 aac ttt ctc cgc gaa gct ctc ttc cga ctc aac aag cgc att gaa atc        1053
Asn Phe Leu Arg Glu Ala Leu Phe Arg Leu Asn Lys Arg Ile Glu Ile
     85                  90                  95 tgg ggc tca gtc gga acg ggc aag ggt cat tgg aag ctg gta aag caa        1101
Trp Gly Ser Val Gly Thr Gly Lys Gly His Trp Lys Leu Val Lys Gln
100                 105                 110
```

-continued

```
              100                 105                 110                 115
gct agc ccg gga aac ctc caa gat gtg gaa gaa gag ttg ggc agc gtt          1149
Ala Ser Pro Gly Asn Leu Gln Asp Val Glu Glu Glu Leu Gly Ser Val
                    120                 125                 130 ggt gga tta tcc atg gac tcg gct cca att atc cta gca gtg aag atc          1197
Gly Gly Leu Ser Met Asp Ser Ala Pro Ile Ile Leu Ala Val Lys Ile
                135                 140                 145 tcg gcc aag gcc gca gag gct agg agt gtg gga gtg tgc ttt gcg gac          1245
Ser Ala Lys Ala Ala Glu Ala Arg Ser Val Gly Val Cys Phe Ala Asp
            150                 155                 160 gca agt gta cgg gaa ctc ggt gtt agc gag ttt ctg gat aac gat atc          1293
Ala Ser Val Arg Glu Leu Gly Val Ser Glu Phe Leu Asp Asn Asp Ile
        165                 170                 175 tat tcc aac ttt gag tcg ctt att atc caa ctc ggg gtg aag gag tgt          1341
Tyr Ser Asn Phe Glu Ser Leu Ile Ile Gln Leu Gly Val Lys Glu Cys
180                 185                 190                 195 ttg gtg cag atg gat gct aat aag aag gat gtt gag ctg gga aag att          1389
Leu Val Gln Met Asp Ala Asn Lys Lys Asp Val Glu Leu Gly Lys Ile
                    200                 205                 210 cgg gct att gcg gat agt tgt ggg atc gct atc tcc gag agg ccg gtg          1437
Arg Ala Ile Ala Asp Ser Cys Gly Ile Ala Ile Ser Glu Arg Pro Val
                215                 220                 225 gct gat tat ggt gtc aag gat att gag cag gat ctg acg agg ttg ttg          1485
Ala Asp Tyr Gly Val Lys Asp Ile Glu Gln Asp Leu Thr Arg Leu Leu
            230                 235                 240 agg gat gaa cgg tcg gct ggt acg ctg ccg cag acg gag cta aag ctt          1533
Arg Asp Glu Arg Ser Ala Gly Thr Leu Pro Gln Thr Glu Leu Lys Leu
        245                 250                 255 gcg atg ggc tcg gcg tct gcg ttg atc aag tac ctt ggg gtt atg acg          1581
Ala Met Gly Ser Ala Ser Ala Leu Ile Lys Tyr Leu Gly Val Met Thr
260                 265                 270                 275 gat cct aca aac ttc ggc cag tac cag ctc tat cag cat gat ttg tcg          1629
Asp Pro Thr Asn Phe Gly Gln Tyr Gln Leu Tyr Gln His Asp Leu Ser
                    280                 285                 290 cag ttt atg aag ttg gat tcg tcg gcg ctg cgt gct ctt aac ctt atg          1677
Gln Phe Met Lys Leu Asp Ser Ser Ala Leu Arg Ala Leu Asn Leu Met
                295                 300                 305 cct ggt ccg cgg gac gga tcg aag tct atg agt ttg ttt ggt ttg ttg          1725
Pro Gly Pro Arg Asp Gly Ser Lys Ser Met Ser Leu Phe Gly Leu Leu
            310                 315                 320 aat cac tgc aag acc cct gtt ggt agc cgg ttg ctt gcg cag tgg ctg          1773
Asn His Cys Lys Thr Pro Val Gly Ser Arg Leu Leu Ala Gln Trp Leu
        325                 330                 335 aaa cag ccg ttg atg gat ctg gcg gag atc gag aag aga cag cag ctt          1821
Lys Gln Pro Leu Met Asp Leu Ala Glu Ile Glu Lys Arg Gln Gln Leu
340                 345                 350                 355 gtt gag gcg ttt gtt gtt aac acg gag ctc aga cag act atg cag gag          1869
Val Glu Ala Phe Val Val Asn Thr Glu Leu Arg Gln Thr Met Gln Glu
                    360                 365                 370 gag cat ctt cgc tcc ata ccg gat ctg tat aga cta gcg aag cgg ttc          1917
Glu His Leu Arg Ser Ile Pro Asp Leu Tyr Arg Leu Ala Lys Arg Phe
                375                 380                 385 cag cgc aaa cag gca aac ttg gaa gac gtt gtg cgg gtg tac cag gtt          1965
Gln Arg Lys Gln Ala Asn Leu Glu Asp Val Val Arg Val Tyr Gln Val
            390                 395                 400 gct att cgt ttg cct ggt ttt gtc aac tct ctc gag aat gtt atg gat          2013
Ala Ile Arg Leu Pro Gly Phe Val Asn Ser Leu Glu Asn Val Met Asp
        405                 410                 415 gaa gag tat cag acg ccc ctg gag acg gag tat act tcc aac ctc cgg          2061
```

-continued

```
Glu Glu Tyr Gln Thr Pro Leu Glu Thr Glu Tyr Thr Ser Asn Leu Arg
420                 425                 430                 435 agt cac tct gat agc tta gcg aaa ctg gag gag atg gtt gag act acg      2109
Ser His Ser Asp Ser Leu Ala Lys Leu Glu Glu Met Val Glu Thr Thr
                440                 445                 450 gtt gac ctt gat gcg ctg gag aac cac gag ttc atc atc aag cct gag      2157
Val Asp Leu Asp Ala Leu Glu Asn His Glu Phe Ile Ile Lys Pro Glu
            455                 460                 465 ttt gac gag agt ctg cgg atc atc agg aag aag ctg gac aag ctc cgt      2205
Phe Asp Glu Ser Leu Arg Ile Ile Arg Lys Lys Leu Asp Lys Leu Arg
        470                 475                 480 cat gat atg ggc gtt gag cac cgc agg gta gct cgg gac ctt gac caa      2253
His Asp Met Gly Val Glu His Arg Arg Val Ala Arg Asp Leu Asp Gln
    485                 490                 495 gat att gag aag aag ttg ttc ctg gag aac cac agg gtg cac gga tgg      2301
Asp Ile Glu Lys Lys Leu Phe Leu Glu Asn His Arg Val His Gly Trp
500                 505                 510                 515 tgc ttc cga ctt act cgc aac gag tcg gga tgc atc cgc aat aag aga      2349
Cys Phe Arg Leu Thr Arg Asn Glu Ser Gly Cys Ile Arg Asn Lys Arg
                520                 525                 530 gag tac cag gaa tgt tct aca cag aag aac ggt gtc tac ttc act acg      2397
Glu Tyr Gln Glu Cys Ser Thr Gln Lys Asn Gly Val Tyr Phe Thr Thr
            535                 540                 545 tcg act atg caa acc ttg cgc cgg gag cat gat caa ctg tcc tcg aac      2445
Ser Thr Met Gln Thr Leu Arg Arg Glu His Asp Gln Leu Ser Ser Asn
        550                 555                 560 tac aat aga act cag acc ggc ctg gtg aat gag gtc gtt aac gtt gcc      2493
Tyr Asn Arg Thr Gln Thr Gly Leu Val Asn Glu Val Val Asn Val Ala
    565                 570                 575 gcg tcc tac tgt cct gtt ttg gaa cga ctt gcc ggt gtc ata gca cac      2541
Ala Ser Tyr Cys Pro Val Leu Glu Arg Leu Ala Gly Val Ile Ala His
580                 585                 590                 595 ctc gat gtc att gta agc ttc gct cat gct tct gtt cat gcg ccg acc      2589
Leu Asp Val Ile Val Ser Phe Ala His Ala Ser Val His Ala Pro Thr
                600                 605                 610 ccc tat gct cgg ccc aag atg cac cca cga ggc acc gga aac aca gtt      2637
Pro Tyr Ala Arg Pro Lys Met His Pro Arg Gly Thr Gly Asn Thr Val
            615                 620                 625 ctc aag gaa gcg cgc cac ccc tgt atg gaa atg cag gat gat att tca      2685
Leu Lys Glu Ala Arg His Pro Cys Met Glu Met Gln Asp Asp Ile Ser
        630                 635                 640 ttc att act aat gat gtg gct ttg gtc cga gac gag tcc tcc ttc ctc      2733
Phe Ile Thr Asn Asp Val Ala Leu Val Arg Asp Glu Ser Ser Phe Leu
    645                 650                 655 atc att act ggt cct aac atg gga ggt aaa tcg act tat att cgc caa      2781
Ile Ile Thr Gly Pro Asn Met Gly Gly Lys Ser Thr Tyr Ile Arg Gln
660                 665                 670                 675 att ggt gtt atc gct ctc atg gct cag acg ggc tgc ttt gtg cct tgt      2829
Ile Gly Val Ile Ala Leu Met Ala Gln Thr Gly Cys Phe Val Pro Cys
                680                 685                 690 aca gaa gca gaa ttg acc atc ttt gac tgt atc ctt gca cgt gtt ggt      2877
Thr Glu Ala Glu Leu Thr Ile Phe Asp Cys Ile Leu Ala Arg Val Gly
            695                 700                 705 gca agt gat tca cag ctc aag gga gtt tcc act ttc atg gct gag atg      2925
Ala Ser Asp Ser Gln Leu Lys Gly Val Ser Thr Phe Met Ala Glu Met
        710                 715                 720 ctc gaa aca tcc aac atc ctc aag tcg gca acg tcc gag tct ctt atc      2973
Leu Glu Thr Ser Asn Ile Leu Lys Ser Ala Thr Ser Glu Ser Leu Ile
    725                 730                 735
```

-continued

| | |
|---|---|
| atc atc gac gag ctt ggg cgc ggt aca agc acg tat gac gga ttc ggc<br>Ile Ile Asp Glu Leu Gly Arg Gly Thr Ser Thr Tyr Asp Gly Phe Gly<br>740                           745                      750                      755 | 3021 |
| cta gca tgg gcc atc tct gaa cac atc gtc aca gag att cgt tgc ttc<br>Leu Ala Trp Ala Ile Ser Glu His Ile Val Thr Glu Ile Arg Cys Phe<br>760                      765                    770 | 3069 |
| ggc ctt ttc gct act cac ttc cat gaa ttg aca gct ctc gcc gat cga<br>Gly Leu Phe Ala Thr His Phe His Glu Leu Thr Ala Leu Ala Asp Arg<br>775                      780                    785 | 3117 |
| tac ccc aag tct gtc aag aac ctg cac gta gtc gcc ttc atc ggc gat<br>Tyr Pro Lys Ser Val Lys Asn Leu His Val Val Ala Phe Ile Gly Asp<br>790                      795                    800 | 3165 |
| ggt act gat gat gac agt gaa gat aag aag tcc aag cgg aac cag gtc<br>Gly Thr Asp Asp Asp Ser Glu Asp Lys Lys Ser Lys Arg Asn Gln Val<br>805                      810                    815 | 3213 |
| act ctt ctg tac cgg gtc gaa cct ggc att tgt gac cag tca ttc ggt<br>Thr Leu Leu Tyr Arg Val Glu Pro Gly Ile Cys Asp Gln Ser Phe Gly<br>820                           825                      830                    835 | 3261 |
| atc cac gtt gcc gaa ttg gtc cgc ttc ccg gag aag gtg gtc aac atg<br>Ile His Val Ala Glu Leu Val Arg Phe Pro Glu Lys Val Val Asn Met<br>840                      845                    850 | 3309 |
| gcc cgc cag aag gca gag gaa ctt gaa gac ttt act tca tcc gaa cag<br>Ala Arg Gln Lys Ala Glu Glu Leu Glu Asp Phe Thr Ser Ser Glu Gln<br>855                      860                    865 | 3357 |
| caa gac cag cag tca tcc atg gcg atc gat aaa tac tcg cag gaa gaa<br>Gln Asp Gln Gln Ser Ser Met Ala Ile Asp Lys Tyr Ser Gln Glu Glu<br>870                      875                    880 | 3405 |
| gtt gag gag ggc agt gcc ctt ctc aaa gcg atg ctg ctg aaa tgg aag<br>Val Glu Glu Gly Ser Ala Leu Leu Lys Ala Met Leu Leu Lys Trp Lys<br>885                      890                    895 | 3453 |
| tcg gag acc gag tcc tct ggt aag gag ttg aca gtg gaa gag aag cga<br>Ser Glu Thr Glu Ser Ser Gly Lys Glu Leu Thr Val Glu Glu Lys Arg<br>900                           905                      910                    915 | 3501 |
| cag atc atg cgt gat ctc gtc aaa gca gat gag aag ctg caa gca aac<br>Gln Ile Met Arg Asp Leu Val Lys Ala Asp Glu Lys Leu Gln Ala Asn<br>920                      925                    930 | 3549 |
| aag gtc ttc cag ggt atc aag gct tta tagattagta tttgcgtctt<br>Lys Val Phe Gln Gly Ile Lys Ala Leu<br>935                      940 | 3596 |
| ttttctttct cggggtcata gcggttcggc gtttggaagg tgtcaatctg tgtatgtgtg | 3656 |
| atctacggac atgaggataa aatgtgtagg gaataatatt atccaaaaat tttcgagtga | 3716 |
| ttgcttcttt ggacatatcg cttaggatta aagtggaaag ggagaaatcc cattcaacta | 3776 |
| tatcgacata agtcacgttg agatcgcgag tctagacgct caccggg | 3823 |

<210> SEQ ID NO 2
<211> LENGTH: 940
<212> TYPE: PRT
<213> ORGANISM: Aspergillus oryzae

<400> SEQUENCE: 2

Met Ser Ser Arg Pro Glu Leu Lys Val Asp Asp Glu Val Gly Phe Ile
1               5                    10                  15

Arg Phe Tyr Arg Ser Leu Ala Ala Asn Ser Asn Asp Glu Thr Ile Arg
               20                    25                    30

Val Phe Asp Arg Gly Asp Trp Tyr Ser Ala His Gly Ala Lys Ala Glu
                    35                    40                    45

Phe Ile Ala Arg Thr Val Tyr Lys Thr Thr Ser Ile Leu Arg Asn Leu
50                      55                    60

-continued

```
Gly Arg Ser Asp Ser Gly Gly Leu Pro Ser Val Thr Met Ser Val Thr
 65                  70                  75                  80

Val Phe Arg Asn Phe Leu Arg Glu Ala Leu Phe Arg Leu Asn Lys Arg
             85                  90                  95

Ile Glu Ile Trp Gly Ser Val Gly Thr Gly Lys Gly His Trp Lys Leu
            100                 105                 110

Val Lys Gln Ala Ser Pro Gly Asn Leu Gln Asp Val Glu Glu Glu Leu
        115                 120                 125

Gly Ser Val Gly Gly Leu Ser Met Asp Ser Ala Pro Ile Ile Leu Ala
    130                 135                 140

Val Lys Ile Ser Ala Lys Ala Ala Glu Ala Arg Ser Val Gly Val Cys
145                 150                 155                 160

Phe Ala Asp Ala Ser Val Arg Glu Leu Gly Val Ser Glu Phe Leu Asp
                165                 170                 175

Asn Asp Ile Tyr Ser Asn Phe Glu Ser Leu Ile Ile Gln Leu Gly Val
            180                 185                 190

Lys Glu Cys Leu Val Gln Met Asp Ala Asn Lys Lys Asp Val Glu Leu
        195                 200                 205

Gly Lys Ile Arg Ala Ile Ala Asp Ser Cys Gly Ile Ala Ile Ser Glu
    210                 215                 220

Arg Pro Val Ala Asp Tyr Gly Val Lys Asp Ile Glu Gln Asp Leu Thr
225                 230                 235                 240

Arg Leu Leu Arg Asp Glu Arg Ser Ala Gly Thr Leu Pro Gln Thr Glu
                245                 250                 255

Leu Lys Leu Ala Met Gly Ser Ala Ser Ala Leu Ile Lys Tyr Leu Gly
            260                 265                 270

Val Met Thr Asp Pro Thr Asn Phe Gly Gln Tyr Gln Leu Tyr Gln His
        275                 280                 285

Asp Leu Ser Gln Phe Met Lys Leu Asp Ser Ser Ala Leu Arg Ala Leu
    290                 295                 300

Asn Leu Met Pro Gly Pro Arg Asp Gly Ser Lys Ser Met Ser Leu Phe
305                 310                 315                 320

Gly Leu Leu Asn His Cys Lys Thr Pro Val Gly Ser Arg Leu Leu Ala
                325                 330                 335

Gln Trp Leu Lys Gln Pro Leu Met Asp Leu Ala Glu Ile Glu Lys Arg
            340                 345                 350

Gln Gln Leu Val Glu Ala Phe Val Val Asn Thr Glu Leu Arg Gln Thr
        355                 360                 365

Met Gln Glu Glu His Leu Arg Ser Ile Pro Asp Leu Tyr Arg Leu Ala
    370                 375                 380

Lys Arg Phe Gln Arg Lys Gln Ala Asn Leu Glu Asp Val Val Arg Val
385                 390                 395                 400

Tyr Gln Val Ala Ile Arg Leu Pro Gly Phe Val Asn Ser Leu Glu Asn
                405                 410                 415

Val Met Asp Glu Glu Tyr Gln Thr Pro Leu Glu Thr Glu Tyr Thr Ser
            420                 425                 430

Asn Leu Arg Ser His Ser Asp Ser Leu Ala Lys Leu Glu Glu Met Val
        435                 440                 445

Glu Thr Thr Val Asp Leu Asp Ala Leu Glu Asn His Glu Phe Ile Ile
    450                 455                 460

Lys Pro Glu Phe Asp Glu Ser Leu Arg Ile Ile Arg Lys Lys Leu Asp
465                 470                 475                 480
```

```
Lys Leu Arg His Asp Met Gly Val Glu His Arg Val Ala Arg Asp
              485                 490                 495

Leu Asp Gln Asp Ile Glu Lys Lys Leu Phe Leu Glu Asn His Arg Val
            500                 505                 510

His Gly Trp Cys Phe Arg Leu Thr Arg Asn Glu Ser Gly Cys Ile Arg
            515                 520                 525

Asn Lys Arg Glu Tyr Gln Glu Cys Ser Thr Gln Lys Asn Gly Val Tyr
        530                 535                 540

Phe Thr Thr Ser Thr Met Gln Thr Leu Arg Arg Glu His Asp Gln Leu
545                 550                 555                 560

Ser Ser Asn Tyr Asn Arg Thr Gln Thr Gly Leu Val Asn Glu Val Val
                565                 570                 575

Asn Val Ala Ala Ser Tyr Cys Pro Val Leu Glu Arg Leu Ala Gly Val
            580                 585                 590

Ile Ala His Leu Asp Val Ile Val Ser Phe Ala His Ala Ser Val His
        595                 600                 605

Ala Pro Thr Pro Tyr Ala Arg Pro Lys Met His Pro Arg Gly Thr Gly
        610                 615                 620

Asn Thr Val Leu Lys Glu Ala Arg His Pro Cys Met Glu Met Gln Asp
625                 630                 635                 640

Asp Ile Ser Phe Ile Thr Asn Asp Val Ala Leu Val Arg Asp Glu Ser
                645                 650                 655

Ser Phe Leu Ile Ile Thr Gly Pro Asn Met Gly Gly Lys Ser Thr Tyr
                660                 665                 670

Ile Arg Gln Ile Gly Val Ile Ala Leu Met Ala Gln Thr Gly Cys Phe
            675                 680                 685

Val Pro Cys Thr Glu Ala Glu Leu Thr Ile Phe Asp Cys Ile Leu Ala
        690                 695                 700

Arg Val Gly Ala Ser Asp Ser Gln Leu Lys Gly Val Ser Thr Phe Met
705                 710                 715                 720

Ala Glu Met Leu Glu Thr Ser Asn Ile Leu Lys Ser Ala Thr Ser Glu
                725                 730                 735

Ser Leu Ile Ile Ile Asp Glu Leu Gly Arg Gly Thr Ser Thr Tyr Asp
                740                 745                 750

Gly Phe Gly Leu Ala Trp Ala Ile Ser Glu His Ile Val Thr Glu Ile
            755                 760                 765

Arg Cys Phe Gly Leu Phe Ala Thr His Phe His Glu Leu Thr Ala Leu
770                 775                 780

Ala Asp Arg Tyr Pro Lys Ser Val Lys Asn Leu His Val Val Ala Phe
785                 790                 795                 800

Ile Gly Asp Gly Thr Asp Asp Ser Glu Asp Lys Lys Ser Lys Arg
            805                 810                 815

Asn Gln Val Thr Leu Leu Tyr Arg Val Glu Pro Gly Ile Cys Asp Gln
            820                 825                 830

Ser Phe Gly Ile His Val Ala Glu Leu Val Arg Phe Pro Glu Lys Val
            835                 840                 845

Val Asn Met Ala Arg Gln Lys Ala Glu Glu Leu Glu Asp Phe Thr Ser
850                 855                 860

Ser Glu Gln Gln Asp Gln Gln Ser Ser Met Ala Ile Asp Lys Tyr Ser
865                 870                 875                 880

Gln Glu Glu Val Glu Glu Gly Ser Ala Leu Leu Lys Ala Met Leu Leu
                885                 890                 895

Lys Trp Lys Ser Glu Thr Glu Ser Ser Gly Lys Glu Leu Thr Val Glu
```

-continued

```
                  900             905             910
Glu Lys Arg Gln Ile Met Arg Asp Leu Val Lys Ala Asp Glu Lys Leu
        915                 920                 925

Gln Ala Asn Lys Val Phe Gln Gly Ile Lys Ala Leu
    930                 935                 940
```

<210> SEQ ID NO 3
<211> LENGTH: 38
<212> TYPE: DNA
<213> ORGANISM: Artificial Sequence
<220> FEATURE:
<223> OTHER INFORMATION: Primer

<400> SEQUENCE: 3
gggaagctgc caggccccag tgtcagcctc ctatgctc            38

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
gagcatagga ggctgacatt ggggcctggc agcttccc            38

<210> SEQ ID NO 5
<211> LENGTH: 38
<212> TYPE: DNA
<213> ORGANISM: Artificial Sequence
<220> FEATURE:
<223> OTHER INFORMATION: Primer

<400> SEQUENCE: 5
gagcatagga ggctgacaat ggggcctggc agcttccc            38

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gagcatagga ggctgacagt ggggcctggc agcttccc            38

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
gagcatagga ggctgacacc ggggcctggc agcttccc            38

<210> SEQ ID NO 8
<211> LENGTH: 40
<212> TYPE: DNA
<213> ORGANISM: Artificial Sequence
<220> FEATURE:
<223> OTHER INFORMATION: Primer

<400> SEQUENCE: 8
gagcatagga ggctgacact gtggggcctg gcagcttccc          40

```
<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
gagcatagga ggctgacacc ggggcctggc agcttccc                              38

<210> SEQ ID NO 10
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (4)..(22)
<223> OTHER INFORMATION: n is a,c, g, or t

<400> SEQUENCE: 10
ggcncarath ggntgyttyg tncc                                             24

<210> SEQ ID NO 11
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = a, c, t, g
<220> FEATURE:
<221> NAME/KEY: misc_feature
<222> LOCATION: (9)..(9)
<223> OTHER INFORMATION: n = a, c, t, g
<220> FEATURE:
<221> NAME/KEY: misc_feature
<222> LOCATION: (12)..(12)
<223> OTHER INFORMATION: n = a, c, t, g
<220> FEATURE:
<221> NAME/KEY: misc_feature
<222> LOCATION: (18)..(18)
<223> OTHER INFORMATION: n = a, c, t, g

<400> SEQUENCE: 11
gcccangcna rnccraancc                                                  20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gctcgaaaca tccaacatcc                                                  20

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
```

-continued gctgtgaatc acttgcacc                                                  19

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
cttcataaac tgcgacaaat catgc                                           25

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
ggaggagcat cttcgc                                                     16

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
ggaacttgaa gactttactt catcc                                           25

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ccagaaactc gctaacacc                                                  19

<210> SEQ ID NO 18
<211> LENGTH: 15
<212> TYPE: DNA
<213> ORGANISM: Artificial Sequence
<220> FEATURE:
<223> OTHER INFORMATION: Primer

<400> SEQUENCE: 18
gtgctttgcg gacgc                                                      15

<210> SEQ ID NO 19
<211> LENGTH: 16
<212> TYPE: DNA
<213> ORGANISM: Artificial Sequence
<220> FEATURE:
<223> OTHER INFORMATION: Primer

<400> SEQUENCE: 19
caggacagta ggacgc                                                     16

<210> SEQ ID NO 20
<211> LENGTH: 17
<212> TYPE: DNA
<213> ORGANISM: Artificial Sequence

```
<220> FEATURE:
<223> OTHER INFORMATION: Primer

<400> SEQUENCE: 20
cgagcgatga actctgc                                                      17

<210> SEQ ID NO 21
<211> LENGTH: 17
<212> TYPE: DNA
<213> ORGANISM: Artificial Sequence
<220> FEATURE:
<223> OTHER INFORMATION: Primer

<400> SEQUENCE: 21
gcgttggtgg attatcc                                                      17

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cgttgcatct atcatatacc                                                   20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
ggtatatgat agatgcaacg c                                                 21

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
ccgcgtctcc aacaagatga atgg                                              24

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ccgctttctc ggggtcatag c                                                 21

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
cctttccact ttaatcctaa gc                                                22
```

```
<210> SEQ ID NO 27
<211> LENGTH: 35
<212> TYPE: DNA
<213> ORGANISM: Artificial Sequence
<220> FEATURE:
<223> OTHER INFORMATION: Primer

<400> SEQUENCE: 27
tctgcgaatc gcttggatcc cgaacgcgac aacac                              35

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28
gagctcagat ctcttaggtt ctggacgaga aga                                33

<210> SEQ ID NO 29
<211> LENGTH: 35
<212> TYPE: DNA
<213> ORGANISM: Artificial Sequence
<220> FEATURE:
<223> OTHER INFORMATION: Primer

<400> SEQUENCE: 29
gttgtcgcgt tcgggatcca agcgattcgc agaag                              35

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
gcaagcgcgc gcaatacatg gtgttttgat cat                                33

<210> SEQ ID NO 31
<211> LENGTH: 1010
<212> TYPE: PRT
<213> ORGANISM: human.p

<400> SEQUENCE: 31
```

Ala Gln Ile Gly Cys Phe Val Pro Cys Glu Ser Ala Glu Val Ser Ile
1               5                   10                  15

Val Asp Cys Ile Leu Ala Arg Val Gly Ala Gly Asp Ser Gln Leu Lys
            20                  25                  30

Gly Val Ser Thr Phe Met Ala Glu Met Leu Glu Thr Ala Ser Ile Leu
        35                  40                  45

Arg Ser Ala Thr Lys Asp Ser Leu Ile Ile Ile Asp Glu Leu Gly Arg
    50                  55                  60

Gly Thr Ser Thr Tyr Asp Gly Phe Gly Leu Ala Trp Met Ala Val Gln
65                  70                  75                  80

Pro Lys Glu Thr Leu Gln Leu Glu Ser Ala Ala Glu Val Gly Phe Val
                85                  90                  95

Arg Phe Phe Gln Gly Met Pro Glu Lys Pro Thr Thr Thr Val Arg Leu
            100                 105                 110

Phe Asp Arg Gly Asp Phe Tyr Thr Ala His Gly Glu Asp Ala Leu Leu
        115                 120                 125

```
Ala Ala Arg Glu Val Phe Lys Thr Gln Gly Val Ile Lys Tyr Met Gly
    130                 135                 140

Pro Ala Gly Ala Lys Asn Leu Gln Ser Val Val Leu Ser Lys Met Asn
145                 150                 155                 160

Phe Glu Ser Phe Val Lys Asp Leu Leu Leu Val Arg Gln Tyr Arg Val
                165                 170                 175

Glu Val Tyr Lys Asn Arg Ala Gly Asn Lys Ala Ser Lys Glu Asn Asp
            180                 185                 190

Trp Tyr Leu Ala Tyr Lys Ala Ser Pro Gly Asn Leu Ser Gln Phe Glu
        195                 200                 205

Asp Ile Leu Phe Gly Asn Asn Asp Met Ser Ala Ser Ile Gly Val Val
    210                 215                 220

Gly Val Lys Met Ser Ala Val Asp Gly Gln Arg Gln Val Gly Val Gly
225                 230                 235                 240

Tyr Val Asp Ser Ile Gln Arg Lys Leu Gly Leu Cys Glu Phe Pro Asp
                245                 250                 255

Asn Asp Gln Phe Ser Asn Leu Glu Ala Leu Leu Ile Gln Ile Gly Pro
            260                 265                 270

Lys Glu Cys Val Leu Pro Gly Gly Glu Thr Ala Gly Asp Met Gly Lys
        275                 280                 285

Leu Arg Gln Ile Ile Gln Arg Gly Gly Ile Leu Ile Thr Glu Arg Lys
    290                 295                 300

Lys Ala Asp Phe Ser Thr Lys Asp Ile Tyr Gln Asp Leu Asn Arg Leu
305                 310                 315                 320

Leu Lys Gly Lys Lys Gly Glu Gln Met Asn Ser Ala Val Leu Pro Glu
                325                 330                 335

Met Glu Asn Gln Val Ala Val Ser Ser Leu Ser Ala Val Ile Lys Phe
            340                 345                 350

Leu Glu Leu Leu Ser Asp Asp Ser Asn Phe Gly Gln Phe Glu Leu Thr
        355                 360                 365

Thr Phe Asp Phe Ser Gln Tyr Met Lys Leu Asp Ile Ala Ala Val Arg
    370                 375                 380

Ala Leu Asn Leu Phe Gln Gly Ser Val Glu Asp Thr Thr Gly Ser Gln
385                 390                 395                 400

Ser Leu Ala Ala Leu Leu Asn Lys Cys Lys Thr Pro Gln Gly Gln Arg
                405                 410                 415

Leu Val Asn Gln Trp Ile Lys Gln Pro Leu Met Asp Lys Asn Arg Ile
            420                 425                 430

Glu Glu Arg Leu Asn Leu Val Glu Ala Phe Val Glu Asp Ala Glu Leu
        435                 440                 445

Arg Gln Thr Leu Gln Glu Asp Leu Leu Arg Arg Phe Pro Asp Leu Asn
    450                 455                 460

Arg Leu Ala Lys Lys Phe Gln Arg Gln Ala Ala Asn Leu Gln Asp Cys
465                 470                 475                 480

Tyr Arg Leu Tyr Gln Gly Ile Asn Gln Leu Pro Asn Val Ile Gln Ala
                485                 490                 495

Leu Glu Lys His Glu Gly Lys His Gln Lys Leu Leu Leu Ala Val Phe
            500                 505                 510

Val Thr Pro Leu Thr Asp Leu Arg Ser Asp Phe Ser Lys Phe Gln Glu
        515                 520                 525

Met Ile Glu Thr Thr Leu Asp Met Asp Gln Val Glu Asn His Glu Phe
    530                 535                 540
```

```
Leu Val Lys Pro Ser Phe Asp Pro Asn Leu Ser Glu Leu Arg Glu Ile
545                 550                 555                 560

Met Asn Asp Leu Glu Lys Lys Met Gln Ser Thr Leu Ile Ser Ala Ala
                565                 570                 575

Arg Asp Leu Gly Leu Asp Pro Gly Lys Gln Ile Lys Leu Asp Ser Ser
                580                 585                 590

Ala Gln Phe Gly Tyr Tyr Phe Arg Val Thr Cys Lys Glu Glu Lys Val
        595                 600                 605

Leu Arg Asn Asn Lys Asn Phe Ser Thr Val Asp Ile Gln Lys Asn Gly
        610                 615                 620

Val Lys Phe Thr Asn Ser Lys Leu Thr Ser Leu Asn Glu Glu Tyr Thr
625                 630                 635                 640

Lys Asn Lys Thr Glu Tyr Glu Ala Gln Asp Ala Ile Val Lys Glu
                645                 650                 655

Ile Val Asn Ile Ser Ser Gly Tyr Val Glu Pro Met Gln Thr Leu Asn
                660                 665                 670

Asp Val Leu Ala Gln Leu Asp Ala Val Ser Phe Ala His Val Ser
                675                 680                 685

Asn Gly Ala Pro Val Pro Tyr Val Arg Pro Ala Ile Leu Glu Lys Gly
690                 695                 700

Gln Gly Arg Ile Ile Leu Lys Ala Ser Arg His Ala Cys Val Glu Val
705                 710                 715                 720

Gln Asp Glu Ile Ala Phe Ile Pro Asn Asp Val Tyr Phe Glu Lys Asp
                725                 730                 735

Lys Gln Met Phe His Ile Ile Thr Gly Pro Asn Met Gly Gly Lys Ser
                740                 745                 750

Thr Tyr Ile Arg Gln Thr Gly Val Ile Val Leu Met Ala Gln Ile Gly
                755                 760                 765

Cys Phe Val Pro Cys Glu Ser Ala Glu Val Ser Ile Val Asp Cys Ile
770                 775                 780

Leu Ala Arg Val Gly Ala Gly Asp Ser Gln Leu Lys Gly Val Ser Thr
785                 790                 795                 800

Phe Met Ala Glu Met Leu Glu Thr Ala Ser Ile Leu Arg Ser Ala Thr
                805                 810                 815

Lys Asp Ser Leu Ile Ile Ile Asp Glu Leu Gly Arg Gly Thr Ser Thr
                820                 825                 830

Tyr Asp Gly Phe Gly Leu Ala Trp Ala Ile Ser Glu Tyr Ile Ala Thr
                835                 840                 845

Lys Ile Gly Ala Phe Cys Met Phe Ala Thr His Phe His Glu Leu Thr
850                 855                 860

Ala Leu Ala Asn Gln Ile Pro Thr Val Asn Asn Leu His Val Thr Ala
865                 870                 875                 880

Leu Thr Thr Glu Glu Thr Leu Thr Met Leu Tyr Gln Val Lys Lys Gly
                885                 890                 895

Val Cys Asp Gln Ser Phe Gly Ile His Val Ala Glu Leu Ala Asn Phe
                900                 905                 910

Pro Lys His Val Ile Glu Cys Ala Lys Gln Lys Ala Leu Glu Leu Glu
                915                 920                 925

Glu Phe Gln Tyr Ile Gly Glu Ser Gln Gly Tyr Asp Ile Met Glu Pro
                930                 935                 940

Ala Ala Lys Lys Cys Tyr Leu Glu Arg Glu Gln Gly Glu Lys Ile Ile
945                 950                 955                 960

Gln Glu Phe Leu Ser Lys Val Lys Gln Met Pro Phe Thr Glu Met Ser
```

```
                            965                 970                 975
Glu Glu Asn Ile Thr Ile Lys Leu Lys Gln Leu Lys Ala Glu Val Ile
                    980                 985                 990
Ala Lys Asn Asn Ser Phe Val Asn Glu Ile Ile Ser Arg Ile Lys Val
                995                 1000                1005
Thr Thr
    1010

<210> SEQ ID NO 32
<211> LENGTH: 1042
<212> TYPE: PRT
<213> ORGANISM: Saccharomyces cerevisiae

<400> SEQUENCE: 32

Ala Gln Ile Gly Cys Phe Val Pro Cys Glu Glu Ala Glu Ile Ala Ile
1               5                   10                  15

Val Asp Ala Ile Leu Cys Arg Val Gly Ala Gly Asp Ser Gln Leu Lys
            20                  25                  30

Gly Val Ser Thr Phe Met Val Glu Ile Leu Glu Thr Ala Ser Ile Leu
        35                  40                  45

Lys Asn Ala Ser Lys Asn Ser Leu Ile Ile Val Asp Glu Leu Gly Arg
    50                  55                  60

Gly Thr Ser Thr Tyr Asp Gly Phe Gly Leu Ala Trp Met Ser Ser Thr
65                  70                  75                  80

Arg Pro Glu Leu Lys Phe Ser Asp Val Ser Glu Glu Arg Asn Phe Tyr
                85                  90                  95

Lys Lys Tyr Thr Gly Leu Pro Lys Lys Pro Leu Lys Thr Ile Arg Leu
            100                 105                 110

Val Asp Lys Gly Asp Tyr Tyr Thr Val Ile Gly Ser Asp Ala Ile Phe
        115                 120                 125

Val Ala Asp Ser Val Tyr His Thr Gln Ser Val Leu Lys Asn Cys Gln
    130                 135                 140

Leu Asp Pro Val Thr Ala Lys Asn Phe His Glu Pro Thr Lys Tyr Val
145                 150                 155                 160

Thr Val Ser Leu Gln Val Leu Ala Thr Leu Leu Lys Leu Cys Leu Leu
                165                 170                 175

Asp Leu Gly Tyr Lys Val Glu Ile Tyr Asp Lys Gly Trp Lys Leu Ile
            180                 185                 190

Lys Ser Ala Ser Pro Gly Asn Ile Glu Gln Val Asn Glu Leu Met Asn
        195                 200                 205

Met Asn Ile Asp Ser Ser Ile Ile Ala Ser Leu Lys Val Gln Trp
    210                 215                 220

Asn Ser Gln Asp Gly Asn Cys Ile Ile Gly Val Ala Phe Ile Asp Thr
225                 230                 235                 240

Thr Ala Tyr Lys Val Gly Met Leu Asp Ile Val Asp Asn Glu Val Tyr
                245                 250                 255

Ser Asn Leu Glu Ser Phe Leu Ile Gln Leu Gly Val Lys Glu Cys Leu
            260                 265                 270

Val Gln Asp Leu Thr Ser Asn Ser Asn Ser Asn Ala Glu Met Gln Lys
        275                 280                 285

Val Ile Asn Val Ile Asp Arg Cys Gly Cys Val Val Thr Leu Leu Lys
    290                 295                 300

Asn Ser Glu Phe Ser Glu Lys Asp Val Glu Leu Asp Leu Thr Lys Leu
305                 310                 315                 320
```

```
Leu Gly Asp Asp Leu Ala Leu Ser Leu Pro Gln Lys Tyr Ser Lys Leu
            325                 330                 335

Ser Met Gly Ala Cys Asn Ala Leu Ile Gly Tyr Leu Gln Leu Leu Ser
            340                 345                 350

Glu Gln Asp Gln Val Gly Lys Tyr Glu Leu Val Glu His Lys Leu Lys
            355                 360                 365

Glu Phe Met Lys Leu Asp Ala Ser Ala Ile Lys Ala Leu Asn Leu Phe
            370                 375                 380

Pro Gln Gly Pro Gln Asn Pro Phe Gly Ser Asn Asn Leu Ala Val Ser
385                 390                 395                 400

Gly Phe Thr Ser Ala Gly Asn Ser Gly Lys Val Thr Ser Leu Phe Gln
            405                 410                 415

Leu Leu Asn His Cys Lys Thr Asn Ala Gly Val Arg Leu Leu Asn Glu
            420                 425                 430

Trp Leu Lys Gln Pro Leu Thr Asn Ile Asp Glu Ile Asn Lys Arg His
            435                 440                 445

Asp Leu Val Asp Tyr Leu Ile Asp Gln Ile Glu Leu Arg Gln Met Leu
450                 455                 460

Thr Ser Glu Tyr Leu Pro Met Ile Pro Asp Ile Arg Arg Leu Thr Lys
465                 470                 475                 480

Lys Leu Asn Lys Arg Gly Asn Leu Glu Asp Val Leu Lys Ile Tyr Gln
            485                 490                 495

Phe Ser Lys Arg Ile Pro Glu Ile Val Gln Val Phe Thr Ser Phe Leu
            500                 505                 510

Glu Asp Asp Ser Pro Thr Glu Pro Val Asn Glu Leu Val Arg Ser Val
            515                 520                 525

Trp Leu Ala Pro Leu Ser His Val Glu Pro Leu Ser Lys Phe Glu
            530                 535                 540

Glu Met Val Glu Thr Thr Val Asp Leu Asp Ala Tyr Glu Glu Asn Asn
545                 550                 555                 560

Glu Phe Met Ile Lys Val Glu Phe Asn Glu Glu Leu Gly Lys Ile Arg
            565                 570                 575

Ser Lys Leu Asp Thr Leu Arg Asp Glu Ile His Ser Ile His Leu Asp
            580                 585                 590

Ser Ala Glu Asp Leu Gly Phe Asp Pro Asp Lys Lys Leu Lys Leu Glu
            595                 600                 605

Asn His His Leu His Gly Trp Cys Met Arg Leu Thr Arg Asn Asp Ala
            610                 615                 620

Lys Glu Leu Arg Lys His Lys Lys Tyr Ile Glu Leu Ser Thr Val Lys
625                 630                 635                 640

Ala Gly Ile Phe Phe Ser Thr Lys Gln Leu Lys Ser Ile Ala Asn Glu
            645                 650                 655

Thr Asn Ile Leu Gln Lys Glu Tyr Asp Lys Gln Gln Ser Ala Leu Val
            660                 665                 670

Arg Glu Ile Ile Asn Ile Thr Leu Thr Tyr Thr Pro Val Phe Glu Lys
            675                 680                 685

Leu Ser Leu Val Leu Ala His Leu Asp Val Ile Ala Ser Phe Ala His
            690                 695                 700

Thr Ser Ser Tyr Ala Pro Ile Pro Tyr Ile Arg Pro Lys Leu His Pro
705                 710                 715                 720

Met Asp Ser Glu Arg Arg Thr His Leu Ile Ser Ser Arg His Pro Val
            725                 730                 735

Leu Glu Met Gln Asp Asp Ile Ser Phe Ile Ser Asn Asp Val Thr Leu
```

-continued

```
                    740                 745                 750
Glu Ser Gly Lys Gly Asp Phe Leu Ile Ile Thr Gly Pro Asn Met Gly
            755                 760                 765

Gly Lys Ser Thr Tyr Ile Arg Gln Val Gly Val Ile Ser Leu Met Ala
770                 775                 780

Gln Ile Gly Cys Phe Val Pro Cys Glu Glu Ala Glu Ile Ala Ile Val
785                 790                 795                 800

Asp Ala Ile Leu Cys Arg Val Gly Ala Gly Asp Ser Gln Leu Lys Gly
                805                 810                 815

Val Ser Thr Phe Met Val Glu Ile Leu Glu Thr Ala Ser Ile Leu Lys
            820                 825                 830

Asn Ala Ser Lys Asn Ser Leu Ile Ile Val Asp Glu Leu Gly Arg Gly
            835                 840                 845

Thr Ser Thr Tyr Asp Gly Phe Gly Leu Ala Trp Ala Ile Ala Glu His
            850                 855                 860

Ile Ala Ser Lys Ile Gly Cys Phe Ala Leu Phe Ala Thr His Phe His
865                 870                 875                 880

Glu Leu Thr Glu Leu Ser Glu Lys Leu Pro Asn Val Lys Asn Met His
                885                 890                 895

Val Val Ala His Ile Glu Lys Asn Leu Lys Glu Gln Lys His Asp Asp
            900                 905                 910

Glu Asp Ile Thr Leu Leu Tyr Lys Val Glu Pro Gly Ile Ser Asp Gln
            915                 920                 925

Ser Phe Gly Ile His Val Ala Glu Val Val Gln Phe Pro Glu Lys Ile
            930                 935                 940

Val Lys Met Ala Lys Arg Lys Ala Asn Glu Leu Asp Asp Leu Lys Thr
945                 950                 955                 960

Asn Asn Glu Asp Leu Lys Lys Ala Lys Leu Ser Leu Gln Glu Val Asn
                965                 970                 975

Glu Gly Asn Ile Arg Leu Lys Ala Leu Leu Lys Glu Trp Ile Arg Lys
            980                 985                 990

Val Lys Glu Glu Gly Leu His Asp Pro Ser Lys Ile Thr Glu Glu Ala
            995                 1000                1005

Ser Gln His Lys Ile Gln Glu Leu Leu Arg Ala Ile Ala Asn Glu
    1010                1015                1020

Pro Glu Lys Glu Asn Asp Asn Tyr Leu Glu Ile Tyr Lys Ser Pro
    1025                1030                1035

Cys Cys Tyr Asn
    1040

<210> SEQ ID NO 33
<211> LENGTH: 935
<212> TYPE: PRT
<213> ORGANISM: mus. p.

<400> SEQUENCE: 33

Met Ala Val Gln Pro Lys Glu Thr Leu Gln Leu Glu Gly Ala Ala Glu
1               5                   10                  15

Ala Gly Phe Val Arg Phe Phe Glu Gly Met Pro Glu Lys Pro Ser Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60
```

-continued

```
Lys Tyr Met Gly Pro Ala Gly Ser Lys Thr Leu Gln Ser Val Val Leu
 65                  70                  75                  80

Ser Lys Met Asn Phe Glu Ser Phe Val Lys Asp Leu Leu Val Arg
                 85                  90                  95

Gln Tyr Arg Val Glu Val Tyr Lys Asn Lys Ala Gly Asn Lys Ala Ser
                100                 105                 110

Lys Glu Asn Glu Trp Tyr Leu Ala Phe Lys Ala Ser Pro Gly Asn Leu
            115                 120                 125

Ser Gln Phe Glu Asp Ile Leu Phe Gly Asn Asn Asp Met Ser Ala Ser
        130                 135                 140

Val Gly Val Met Gly Ile Lys Met Ala Val Val Asp Gly Gln Arg His
145                 150                 155                 160

Val Gly Val Gly Tyr Val Asp Ser Thr Gln Arg Lys Leu Gly Leu Cys
                165                 170                 175

Glu Phe Pro Glu Asn Asp Gln Phe Ser Asn Leu Glu Ala Leu Leu Ile
                180                 185                 190

Gln Ile Gly Pro Lys Glu Cys Val Leu Pro Gly Gly Glu Thr Thr Gly
            195                 200                 205

Asp Met Gly Lys Leu Arg Gln Val Ile Gln Arg Gly Ile Leu Ile
        210                 215                 220

Thr Glu Arg Lys Arg Ala Asp Phe Ser Thr Lys Asp Ile Tyr Gln Asp
225                 230                 235                 240

Leu Asn Arg Leu Leu Lys Gly Lys Lys Gly Glu Gln Ile Asn Ser Ala
                245                 250                 255

Ala Leu Pro Glu Met Glu Asn Gln Val Ala Val Ser Ser Leu Ser Ala
                260                 265                 270

Val Ile Lys Phe Leu Glu Leu Leu Ser Asp Asp Ser Asn Phe Gly Gln
            275                 280                 285

Phe Glu Leu Ala Thr Phe Asp Phe Ser Gln Tyr Met Lys Leu Asp Met
        290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Ala
                325                 330                 335

Gln Gly Gln Arg Leu Val Asn Gln Trp Ile Lys Gln Pro Leu Met Asp
            340                 345                 350

Arg Asn Arg Ile Glu Glu Arg Leu Asn Leu Val Glu Ala Phe Val Glu
        355                 360                 365

Asp Ser Glu Leu Arg Gln Ser Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Ser
                405                 410                 415

Val Ile Gln Ala Leu Glu Lys Tyr Glu Gly Arg His Gln Ala Leu Leu
            420                 425                 430

Leu Ala Val Phe Val Thr Pro Leu Ile Asp Leu Arg Ser Asp Phe Ser
        435                 440                 445

Lys Phe Gln Glu Met Ile Glu Thr Thr Leu Asp Met Asp Gln Val Glu
    450                 455                 460

Asn His Glu Phe Leu Val Lys Pro Ser Phe Asp Pro Asn Leu Ser Glu
465                 470                 475                 480

Leu Arg Glu Val Met Asp Gly Leu Glu Lys Lys Met Gln Ser Thr Leu
```

-continued

```
                485                 490                 495
Ile Asn Ala Ala Arg Gly Leu Gly Leu Asp Pro Gly Lys Gln Ile Lys
            500                 505                 510
Leu Asp Ser Ser Ala Gln Phe Gly Tyr Tyr Phe Arg Val Thr Cys Lys
        515                 520                 525
Glu Glu Lys Val Leu Arg Asn Asn Lys Asn Phe Ser Thr Val Asp Ile
    530                 535                 540
Gln Lys Asn Gly Val Lys Phe Thr Asn Ser Glu Leu Ser Ser Leu Asn
545                 550                 555                 560
Glu Glu Tyr Thr Lys Asn Lys Gly Glu Tyr Glu Ala Gln Asp Ala
                565                 570                 575
Ile Val Lys Glu Ile Val Asn Ile Ser Ser Gly Tyr Val Glu Pro Met
            580                 585                 590
Gln Thr Leu Asn Asp Val Leu Ala His Leu Asp Ala Ile Val Ser Phe
        595                 600                 605
Ala His Val Ser Asn Ala Ala Pro Val Pro Tyr Val Arg Pro Val Ile
    610                 615                 620
Leu Glu Lys Gly Lys Gly Arg Ile Ile Leu Lys Ala Ser Arg His Ala
625                 630                 635                 640
Cys Val Glu Val Gln Asp Glu Val Ala Phe Ile Pro Asn Asp Val His
                645                 650                 655
Phe Glu Lys Asp Lys Gln Met Phe His Ile Ile Thr Gly Pro Asn Met
            660                 665                 670
Gly Gly Lys Ser Thr Tyr Ile Arg Gln Thr Gly Val Ile Val Leu Met
        675                 680                 685
Ala Gln Ile Gly Cys Phe Val Pro Cys Glu Ser Ala Glu Val Ser Ile
    690                 695                 700
Val Asp Cys Ile Leu Ala Arg Val Gly Ala Gly Asp Ser Gln Leu Lys
705                 710                 715                 720
Gly Val Ser Thr Phe Met Ala Glu Met Leu Glu Thr Ser Ser Ile Leu
                725                 730                 735
Arg Ser Ala Thr Lys Asp Ser Leu Ile Ile Ile Asp Glu Leu Gly Arg
            740                 745                 750
Gly Thr Ser Thr Tyr Asp Gly Phe Gly Leu Ala Trp Ala Ile Ser Asp
        755                 760                 765
Tyr Ile Ala Thr Lys Ile Gly Ala Phe Cys Met Phe Ala Thr His Phe
    770                 775                 780
His Glu Leu Thr Ala Leu Ala Asn Gln Ile Pro Thr Val Asn Asn Leu
785                 790                 795                 800
His Val Thr Ala Leu Thr Thr Glu Glu Thr Leu Thr Met Leu Tyr Gln
                805                 810                 815
Val Lys Lys Gly Val Cys Asp Gln Ser Phe Gly Ile His Val Ala Glu
            820                 825                 830
Leu Ala Asn Phe Pro Arg His Val Ile Ala Cys Ala Lys Gln Lys Ala
        835                 840                 845
Leu Glu Leu Glu Glu Phe Gln Asn Ile Gly Thr Ser Leu Gly Cys Asp
    850                 855                 860
Glu Ala Glu Pro Ala Ala Lys Arg Arg Cys Leu Glu Arg Glu Gln Gly
865                 870                 875                 880
Glu Lys Ile Ile Leu Glu Phe Leu Ser Lys Val Lys Gln Val Pro Phe
                885                 890                 895
Thr Ala Met Ser Glu Glu Ser Ile Ser Ala Lys Leu Lys Gln Leu Lys
            900                 905                 910
```

```
Ala Glu Val Val Ala Lys Asn Asn Ser Phe Val Asn Glu Ile Ile Ser
        915                 920                 925

Arg Ile Lys Ala Pro Ala Pro
    930             935
```